US008262656B2

(12) United States Patent
Mirza et al.

(10) Patent No.: US 8,262,656 B2
(45) Date of Patent: Sep. 11, 2012

(54) EXTERNAL FIXATION DEVICE FOR FRACTURES

(75) Inventors: Ather Mirza, Smithtown, NY (US); Romi Mirza, Smithtown, NY (US)

(73) Assignee: A.M. Surgical, Inc., Smithtown, NY (US)

( * ) Notice: Subject to any disclaimer, the term of this patent is extended or adjusted under 35 U.S.C. 154(b) by 730 days.

(21) Appl. No.: 12/371,314

(22) Filed: Feb. 13, 2009

(65) Prior Publication Data
US 2009/0187189 A1 Jul. 23, 2009

Related U.S. Application Data

(63) Continuation-in-part of application No. 10/933,578, filed on Sep. 3, 2004, now Pat. No. 7,828,801.

(51) Int. Cl.
*A61B 17/56* (2006.01)
(52) U.S. Cl. ........................................ 606/54
(58) Field of Classification Search ............... 606/79, 606/80, 84, 85, 170, 180; 433/104; 384/100
See application file for complete search history.

(56) References Cited

U.S. PATENT DOCUMENTS

| 1,789,060 | A |   | 1/1931  | Weisenbach |        |
|-----------|---|---|---------|------------|--------|
| 2,333,033 | A |   | 10/1943 | Mraz       |        |
| 2,391,537 | A | * | 12/1945 | Anderson   | 606/59 |
| 2,435,850 | A |   | 2/1948  | Siebrandt  |        |
| 4,135,505 | A |   | 1/1979  | Day        |        |
| 4,271,832 | A |   | 6/1981  | Evans et al. |      |
| 4,299,202 | A |   | 11/1981 | Mayo et al. |      |
| 4,299,212 | A |   | 11/1981 | Goudfrooy  |        |
| 4,488,542 | A |   | 12/1984 | Helland    |        |
| 4,611,586 | A |   | 9/1986  | Agee et al. |      |
| 4,922,896 | A |   | 5/1990  | Agee et al. |      |
| 5,728,096 | A |   | 3/1998  | Faccioli et al. |   |
| 5,951,556 | A |   | 9/1999  | Faccioli et al. |   |
| 6,991,612 | B2|   | 1/2006  | Scheinberg et al. | |
| 7,169,149 | B1| * | 1/2007  | Hajianpour | 606/54 |
| 2006/0064087 | A1 |  | 3/2006 | Mirza et al. |    |
| 2007/0162131 | A1 | * | 7/2007 | Friedman et al. | 623/17.11 |
| 2007/0293864 | A1 |  | 12/2007 | Reimels et al. |  |

OTHER PUBLICATIONS

International Preliminary Report on Patentability (Chapter I of PCT). Mailed Aug. 25, 2011. Application No. PCT/US2009/062182, filed Oct. 27, 2009.
International Search Report and Written Opinion of the International Searching Authority (International Application No. PCT/US2009/062182, filed Oct. 27, 2009).
MacDermid, J.C., "Responsiveness of the disability of the arm, shoulder, and hand (DASH) and patient-rated wrist/hand evaluation (PRWHE) in evaluating change after hand therapy", J. Hand Ther., vol. 17, pp. 18-23 (2004).

(Continued)

*Primary Examiner* — Eduardo C Robert
*Assistant Examiner* — David Comstock
(74) *Attorney, Agent, or Firm* — Ping Wang; Andrews Kurth, LLP

(57) ABSTRACT

An external fixation device for the setting and corrective treatment of bone fractures is disclosed. The device comprises a splint member having a first and a second axially slidable and mutually fastenable base portions for adjusting the length of the splint member and a plurality of bone pins. Each of the base portions of the splint member includes mountings for the bone pins to traverse the site of the bone fracture in a multi-angle and multi-planar pin configuration, so as to permit direct fixation of the fracture and provide a significant degree of stability.

34 Claims, 20 Drawing Sheets

OTHER PUBLICATIONS

Beaton, D.E., et al., "Measuring the whole or the parts? Validity, reliability, and responsiveness of the Disabilities of the Arm, Shoulder and Hand outcome measure in different regions of the upper extremity", J. Hand Ther., vol. 14 pp. 128-146 (2001) (abstract only).

Muller, M.E., "Classification of fractures-long bones", Berlin: Springer-Verlag, pp. 106-115 (1987).

Flinkkila. T., et al., "Poor interobserver reliability of AO classification of fractures of the distal radius", J Bone Joint Surg [Br], vol. 80-B, pp. 670-672 (1998).

Kreder, H.J., et al., "Consistency of AO fracture classification for the distal radius", J. Bone Joint Surg. [Br], vol. 78, pp. 726-731 (1996).

Cole, R.J., et al., "Radiographic evaluation of osseous displacement following intra-articular fractures of the distal radius: Reliability of plain radiography versus computed tomography", J. Hand Surg., vol. 22, pp. 792-800 (1997).

Kreder, H.J., et al., "X-ray film measurements for healed distal radius fractures", J. Hand Surg., vol. 21, pp. 31-39 (1996).

MacDermid, J.C., et al., "Pain and disability reported in the year following a distal radius fracture: A cohort study", BMC Musculoskeletal Disorders, vol. 4, pp. 1-13 (2003).

Knirk, J.L., et al., "Intra-articular fractures of the distal end of the radius in young adults", J Bone Joint Surg, vol. 68, pp. 647-659 (1986).

McQueen, M., et al., "Colles fracture: does the anatomical result affect the final function?", J Bone Joint Surg, vol. 70-B, pp. 649-651 (1988).

MacDermid, J.C., et al., "Patient rating of wrist pain and disability: a reliable and valid measurement tool", J Orthop Trauma, vol. 12, pp. 577-586 (1998).

MacDermid, J.C., et al., "Responsiveness of the short form-36, disability of the arm, shoulder, and hand questionnaire, patient-rated wrist evaluation, and physical impairment measurements in evaluating recovery after a distal radius fracture", J Hand Surg, vol. 25, pp. 330-340 (2000).

Strauss, E.J., et al., "Evaluation of a novel, nonspanning external fixator for treatment of unstable extra-articular fractures of the distal radius: biomechanical comparison with a volar locking plate", J Trauma, vol. 64, pp. 975-981 (2008).

Fernandez, D.L., et al., "Fractures of the Distal Radius: A practical approach to management (second edition)", Springer-Verlag, pp. 58-60 (2002).

Azegami, S., "Radiological evaluation of distal radius fracture: what junior doctors want to know", Orthogate (2008).

Rogge, R., et al., "An analysis of bone stresses and fixation stability using a finite element model of simulated distal radius fractures", J Hand Burg, vol. 27, pp. 86-92 (2002).

Graham, T.J., "Biochemical aspects of percutaneous pinning for distal redial fractures", Fractures of the distal radius (First Edition), pp. 28-36 (1995).

* cited by examiner

EXTERNAL FIXATION DEVICE FOR FRACTURES

This application is a continuation-in-part application of U.S. patent application Ser. No. 10/933,578, filed Sep. 3, 2004 now U.S. Pat. No. 7,828,801. The entirety of all of the aforementioned applications is incorporated herein by reference.

FIELD

The present invention generally relates to a medical device and, in particular, to a percutaneous cross-pin fixation and a non-bridging external fixation device designed for the setting and corrective treatment of bone fractures.

BACKGROUND

Bone fractures are typically treated by restoring the fractured pieces of bone to their natural positions and maintaining those positions while the bone heals. Briefly, the fractured bone(s) is aligned in good position (also called reduction) and then immobilized with a cast that holds the bones in position and immobilizes the joints above and below the fracture. When the initial post-fracture edema or swelling goes down, the fracture may be placed in a removable brace or orthosis. In cases of complex or open fractures, surgical nails, screws, plates and wires may be used to internally hold the fractured bone together. The surgical implantation of these internal fixation devices, however, may cause extensive trauma to the patient, increase potential for infection, and require second surgery for their removal. An alternative to internal fixation devices is the external fixation device. Pins or screws are placed into the broken bone above and below the fracture site to reposition and immobilize the bone fragments. The pins or screws are connected to a metal bar or bars outside the skin to form a stabilizing frame that holds the bones in the proper position so they can heal. After an appropriate period of time, the external fixation device is removed.

Distal radius fracture is a common fracture found in many slip-and-fall cases. Since distal radius fractures have a tendency to collapse, maintenance of fracture reduction is of great significance. Although many external fixation devices have been developed for the treatment of bone fractures, for example in U.S. Pat. No. 1,789,060, U.S. Pat. No. 2,333,033, U.S. Pat. No. 2,435,850, U.S. Pat. No. 4,135,505, U.S. Pat. No. 4,271,832, U.S. Pat. No. 4,299,202, U.S. Pat. No. 4,488,542, U.S. Pat. No. 4,922,896, U.S. Pat. No. 5,728,096 and U.S. Pat. No. 5,951,556, these devices are generally cumbersome and expensive, and are difficult to be readily employed in a restricted spatial area, such as the wrist. There still exists a need for lightweight, non-bridging external fixation devices that allows for direct fixation of a distal radius fracture, maintenance of the radiological parameters, and early mobilization of the wrist.

SUMMARY

An external fixation device for the setting and corrective treatment of a bone fracture is disclosed. The device includes a splint member having a first and a second axially slidable and mutually fastenable base portions for adjusting the length of the splint member and a plurality of bone pins. Each of the base portions of the splint member contains mountings for the bone pins to traverse the site of the bone fracture in a multi-angle and multi-planar configuration so as to secure fractured bone segments against rotation and axial movement. The splint member is made of a fiber reinforced lightweight polymeric material.

In one embodiment, the polymeric material is selected from the group consisting of PPS (polyphenylene sulfide), PEEK (polyetherether ketone), Ultrapek (polyether ketone ether ketone), epoxy, polyester, polyamide, and vinyl ester.

In another embodiment, the fiber is selected from the group consisting of carbon fibers, glass fibers, metal fibers, synthetic fibers, and mixtures thereof.

In another embodiment, the fiber reinforced polymeric material is a carbon-fiber reinforced plastic.

In a related embodiment, the carbon-fiber reinforced plastic has a minimal tensile strength equal to or greater than 30 Ksi.

In another related embodiment, the carbon-fiber reinforced plastic is PPS reinforced with 40-60% of carbon fiber.

In another related embodiment, the carbon-fiber reinforced plastic is PEEK reinforced with 30-50% of carbon fiber.

In another related embodiment, the carbon-fiber reinforced plastic is epoxy reinforced with 30-60% of carbon fiber.

Also disclosed is a method for treating a distal radius fracture. The method involves inserting a first bone pin through the fracture site, joining a first base portion of a splint member with the first bone pin, inserting a second bone pin through the fracture site, jointing a second base portion of the splint member with the second bone pin, positioning and joining the first base portion with the second base portion of the splint member, and inserting one or more bone pins into the fracture site through the first base portion, the second base portion, or both base portions of the splint member. Wherein the bone pins traverse the site of the bone fracture in a multi-angle and multi-planar configuration so as to secure fractured bone segments against rotation and axial movement. In one embodiment, the splint member allows for insertion of up to six bone pins into the fracture site. In another embodiment, the splint member is made of a reinforced lightweight polymeric material.

BRIEF DESCRIPTION OF THE DRAWINGS

Reference may now be made to the following detailed description of a preferred embodiment of the invention, taken in conjunction with the accompanying drawings; in which:

FIG. 15A: PA view. FIG. 15B: Lateral view.

DETAILED DESCRIPTION

Figure 1:
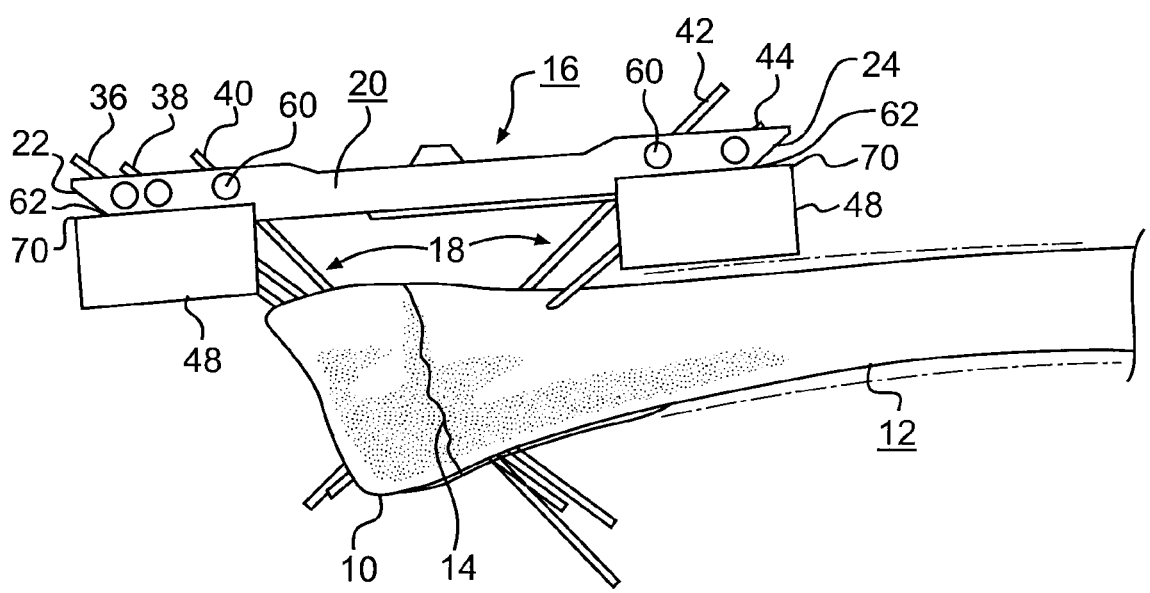
FIG. 1 is a diagrammatic illustration of an embodiment of the external fixation device of the present invention with positioning spacers.

Referring now to FIG. 1, there is illustrated the distal radius portion 10 of the forearm 12 of a patient showing a fracture site 14, which extends through the distal radius portion of the forearm proximate the wrist. In order to impart an immobilization to the fracture site 14, there is provided the inventive external fixation device 16, which, in this instance, employs a novel cross-pin arrangement 18 for fracture fixation without having to immobilize the wrist portion of the patient, thereby avoiding the effects of Ligamentotaxis, which could unduly cause a high degree of discomfort to the patient and also necessitate a lengthy period of rehabilitation in order to again attain full mobility of the wrist joint at the injured site.

In particular, the basically orthopaedic wrist external fixation device 16 (also referred to as the cross-pin fixation (CPX) system) includes an axially adjustable splint 20. The splint 20 is generally rectangular in transverse cross-section and comprises an elongated distal base portion 22 and an elongated proximal base portion 24. The base portions 22 and 24 are slidably interengagable and mutually lockable, and can be adjusted relative to each other to fit the size of the forearm 12 and the specific location of the distal radius fracture site 14 of the patient. Each of the base portions 22, 24 includes a plurality of angularly extending through holes 26, 28, 30, 32, 34 that orient from the top to the bottom of the base portion. The holes 26, 28, 30 in the distal base portion 22 are angled in a direction towards the proximal base portion 24. The holes 32, 34 in the proximal base portion 24 are angled so as to slope or incline towards the distal base portion 22. Bone fracture-setting pins 36, 38, 40, 42, 44 are inserted into the fracture site 14 through the holes 26, 28, 30, 32, 34 to form a rigid lattice-type pin arrangement 18 within the fracture site 14. The rigid lattice-type pin arrangement 18 promotes the healing process by immobilizing the fractured distal radius, maintaining the correct bone alignment, securing the bones against mutual rotation, and minimizing the discomfort to the patient. During the assembling process, the splint structure 20 is kept at an appropriate distance from the skin of the forearm 12 by detachable positioning spacers 48, which are mounted at the spaced apart ends of the distal and proximal base portions 22, 24 through mating guideways or slots formed in the sides of the base portions 22, 24.

The splint 20 is made from a high strength material. In one embodiment, the splint 20 is made of a reinforced lightweight polymeric material. Examples of the polymeric material include, but are not limited to, PPS (polyphenylene sulfide), PEEK (polyetherether ketone), Ultrapek (polyether ketone ether ketone), epoxy, polyester, polyamide, vinyl ester. The polymeric material may be reinforced with carbon fibers, glass fibers, metal fibers such as aluminium fibers, synthetic fibers such as Kevlar, mixtures of the above-described fibers, and minerals such as talc, silica, silicon carbide, zirconia, and alumina. The amount of reinforcement fibers or minerals may constitute 10% (w/w) to 80% (w/w) of the final composition. In one embodiment, the splint 20 is made from carbon-fiber reinforced plastic with a minimal tensile strength of about 30 Ksi.

In a preferred embodiment, the splint 20 is made from PPS reinforced with 40-60% of carbon fiber.

In another preferred embodiment, the splint 20 is made from PEEK reinforced with 30-50% of carbon fiber.

In another preferred embodiment, the splint 20 is made from PEEK reinforced with 30-50% of carbon fiber.

In yet another preferred embodiment, the splint 20 is made from epoxy reinforced with 30-60% of carbon fiber.

In another embodiment, the splint 20 is made of a ceramic material, such as alumina, zirconia, or silicon carbide.

In another embodiment, the splint 20 is made of a lightweight metal or alloy. Examples of lightweight metal and alloy include, but are not limited to, titanium, aluminum and nickel. Examples of alloys include, but are not limited to alloys of titanium, aluminum, zirconium, tantalum, or niobium.

In another embodiment, the splint 20 is made of steel or steel alloys.

The bone fracture-setting pins 36, 38, 40, 42, 44 are also made of a high strength material. Examples of such material include, but are not limited to, surgical grade steel, titanium, and titanium alloys. In one embodiment, the pins are standard 1.6 mm Kirschner wires (K wires).

Figure 2:
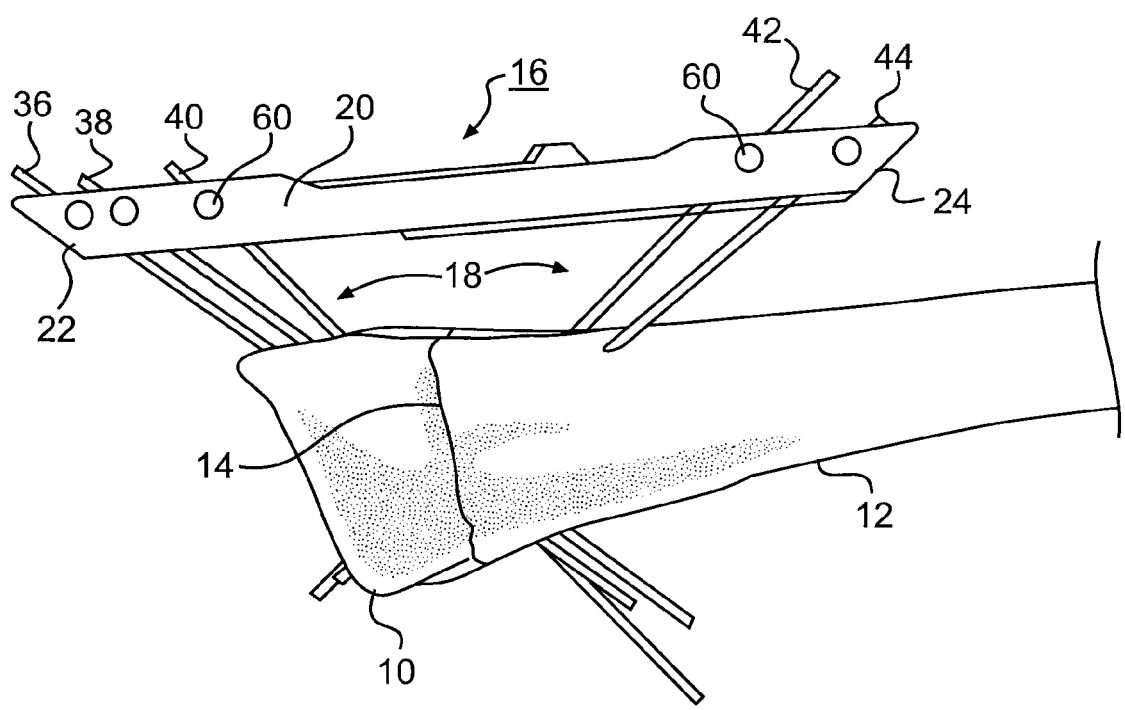
FIG. 2 is a diagrammatic illustration of an embodiment of the external fixation device of the present invention without positioning spacers.

As shown in FIG. 2, upon completing the appropriate positioning of the external fixation device 16 and the arrangement 18 of the pins. The pins are locked in the holes of the splint 20. The positioning spacers 48 are removed by simply sliding off the mating guideways or slots on the base portions 22 and 24. The external arm area about the entire fracture site may be suitably bandaged, as is well known in the medical technology.

Figure 3:
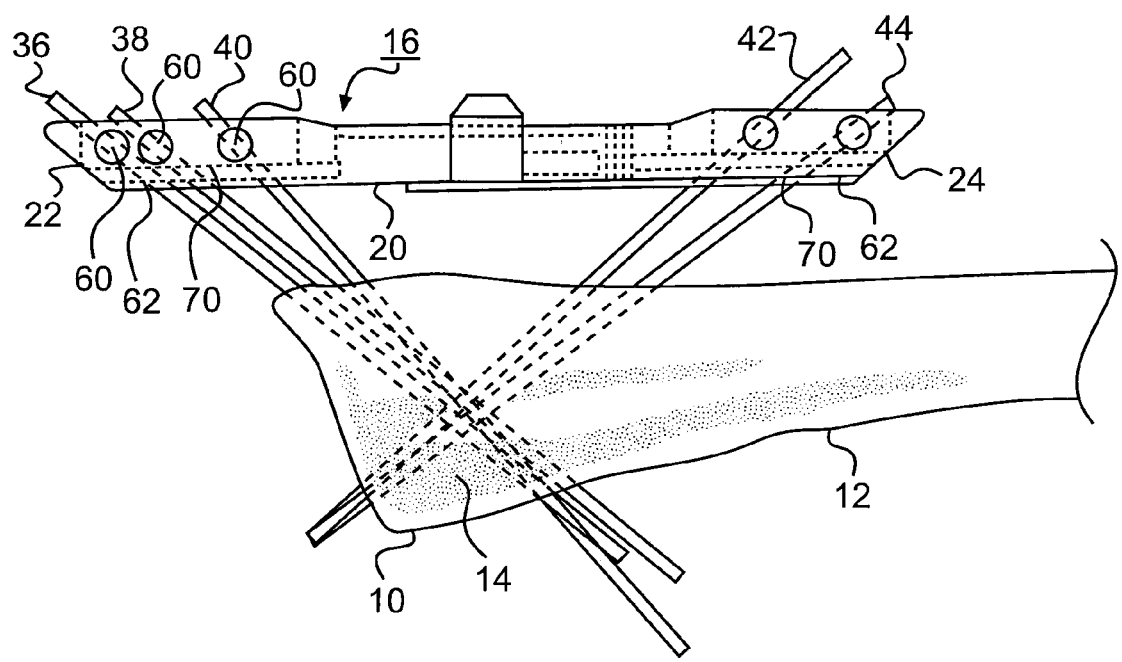
FIG. 3 is a computerized schematic representation showing the external fixation device as attached to a fractured distal radial portion of the forearm.
Figure 4:
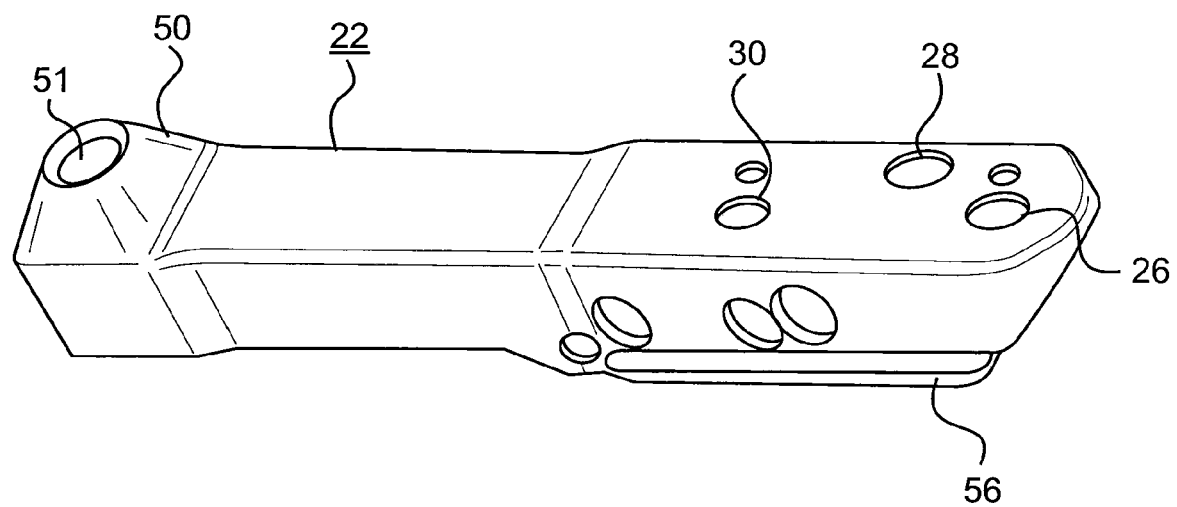
FIG. 4 is a top and side perspective view of an embodiment of the distal base portion of the external fixation device.
Figure 5:
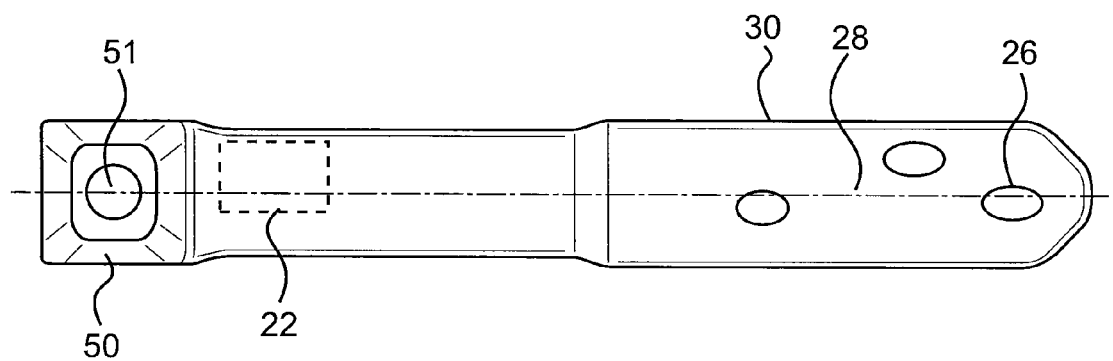
FIG. 5 is a top plan view of an embodiment of the distal base portion of the external fixation device.
Figure 6:
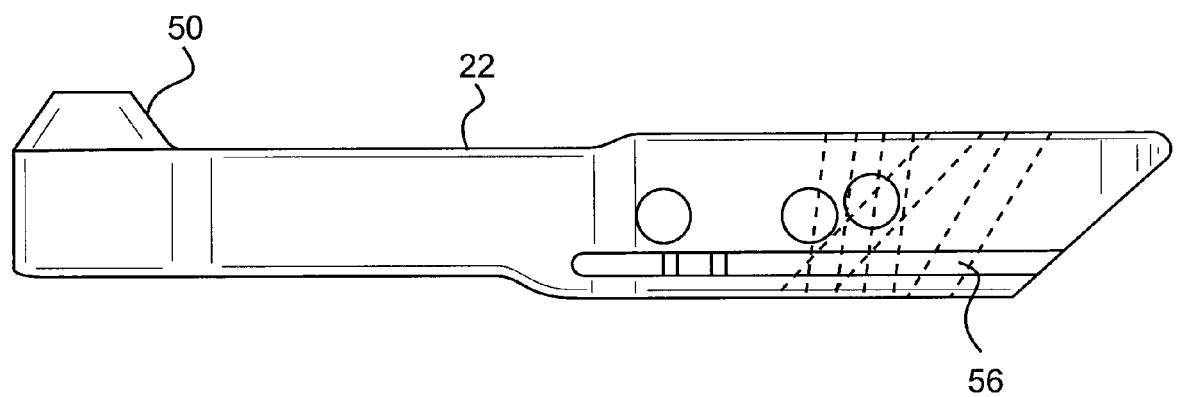
FIG. 6 is a side view of an embodiment of the distal base portion of the external fixation device.
Figure 7:
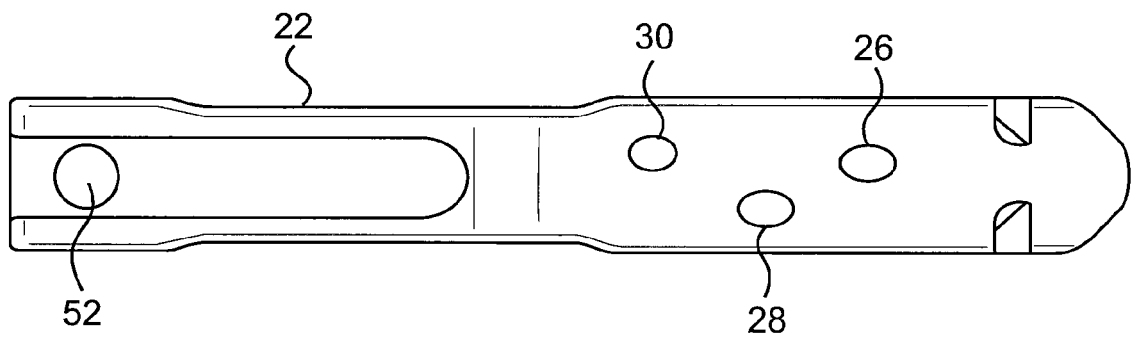
FIG. 7 is a bottom plan view of an embodiment of the distal base portion of the external fixation device.
Figure 8:
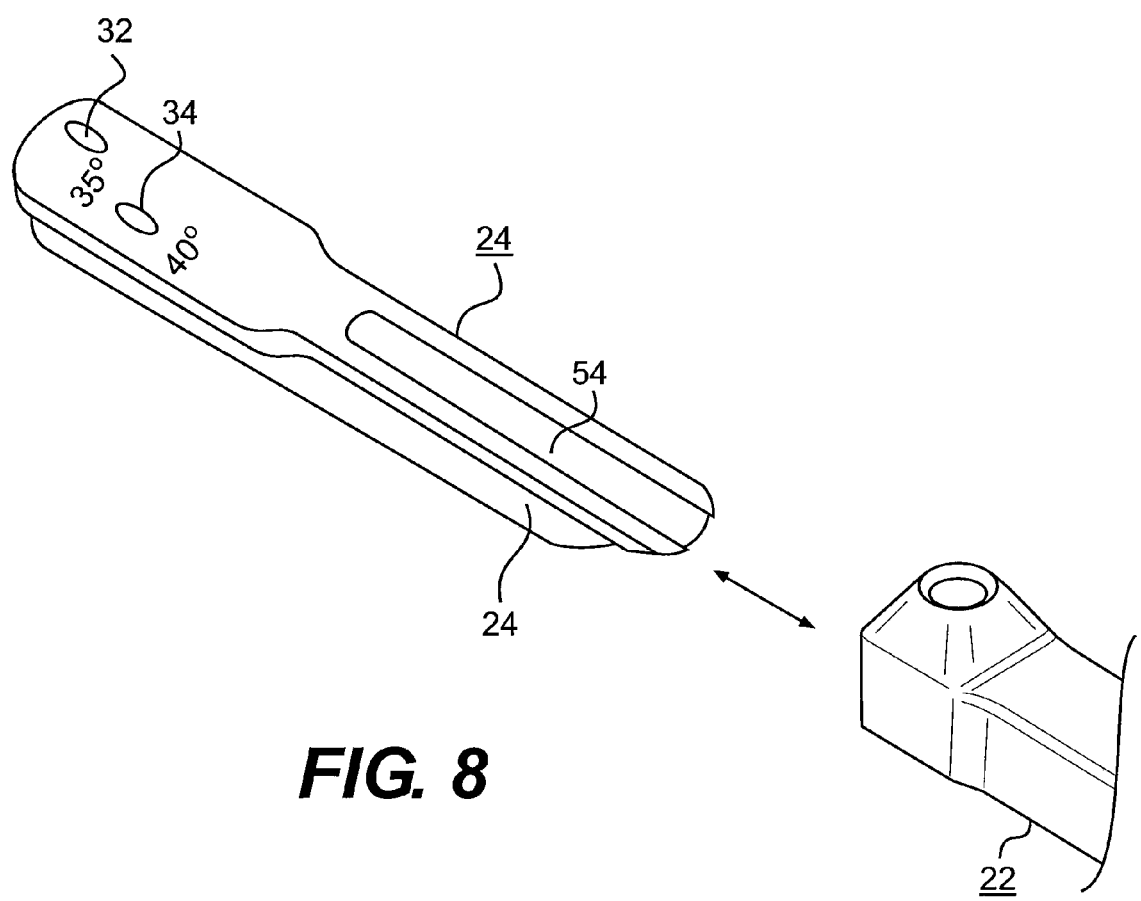
FIG. 8 is a side and perspective view of an embodiment of the proximal base portion of the external fixation device, which can be adaptable and slidably interconnected with the distal base portion of the external fixation device.
Figure 9:
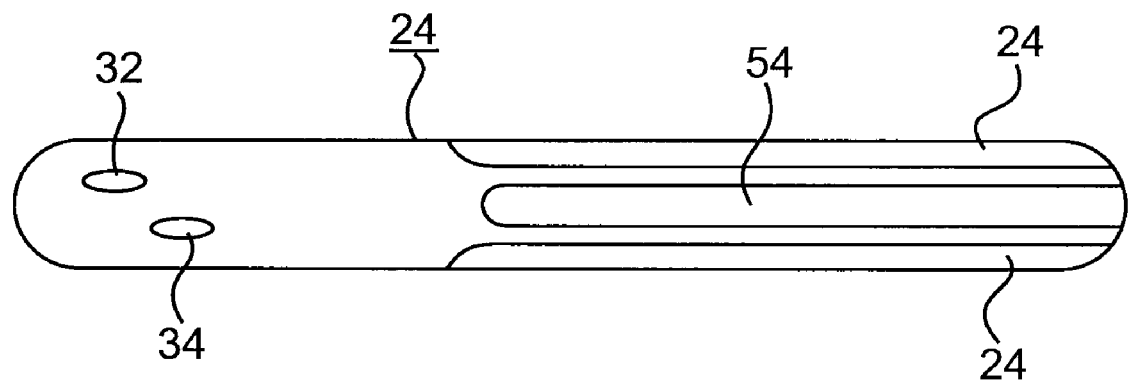
FIG. 9 is a top plan view of an embodiment of the proximate base portion of the external fixation device.
Figure 10:
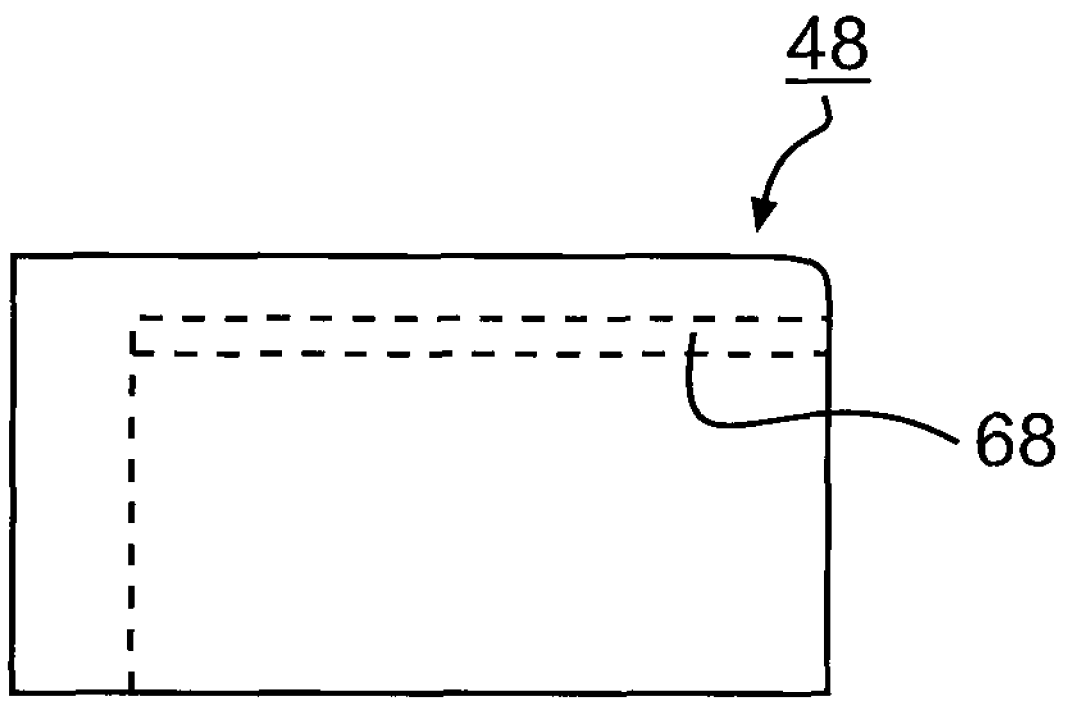
FIGS. 10-13 are, respectively, top, side, bottom and end views of an embodiment of a positioning spacer for deploying the external fixation device.
Figure 11:
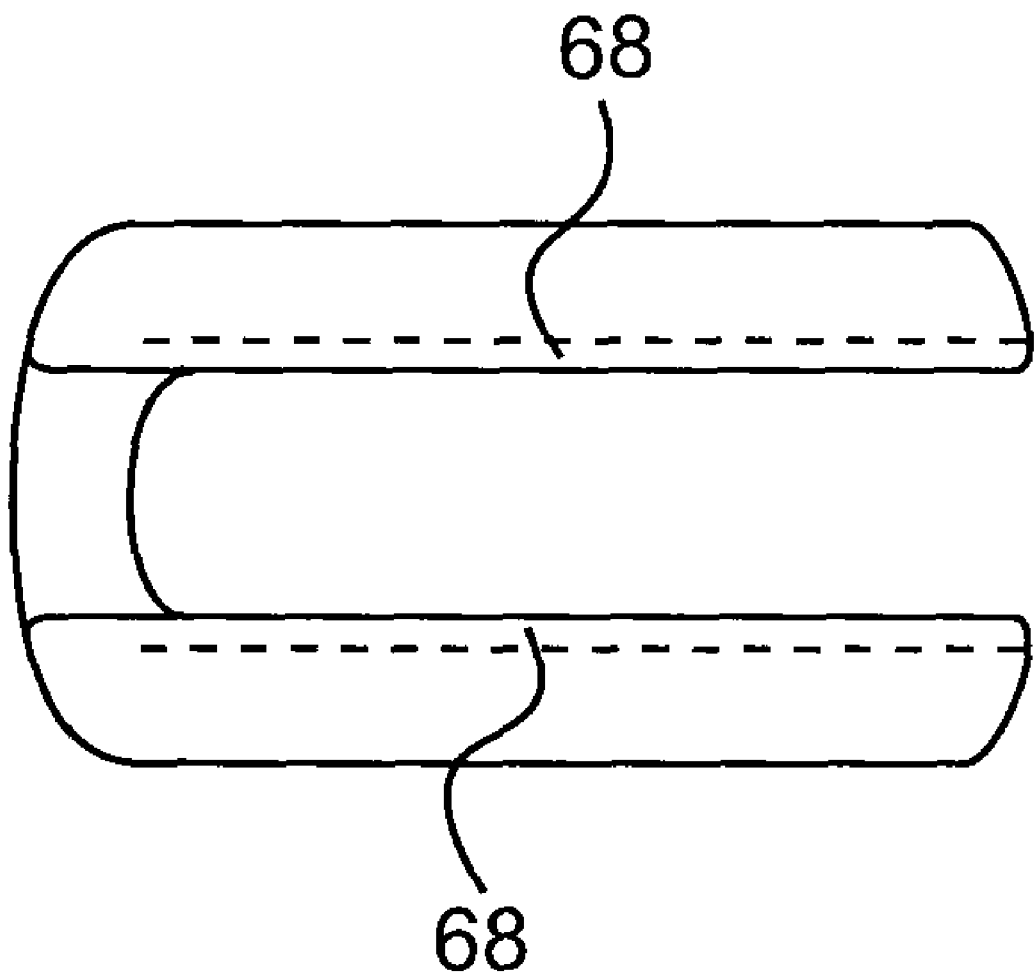
Figure 12:
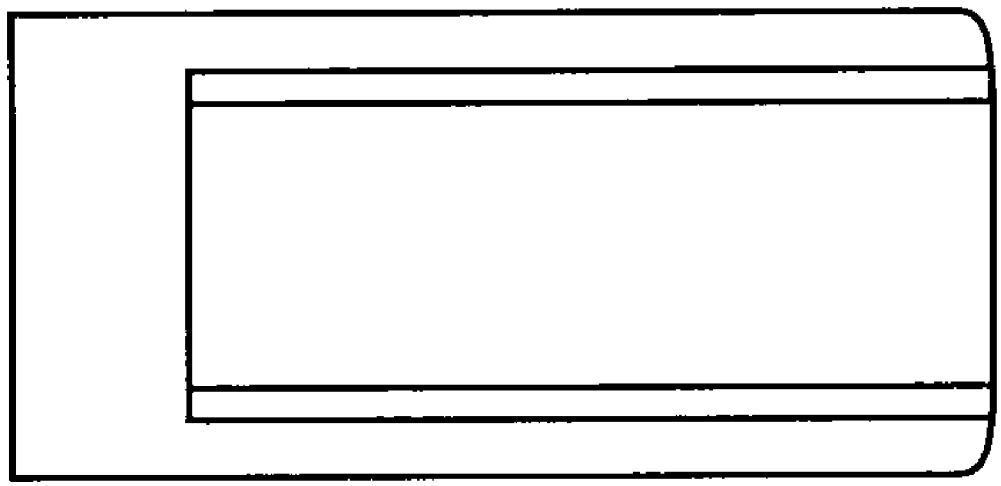
Figure 13:
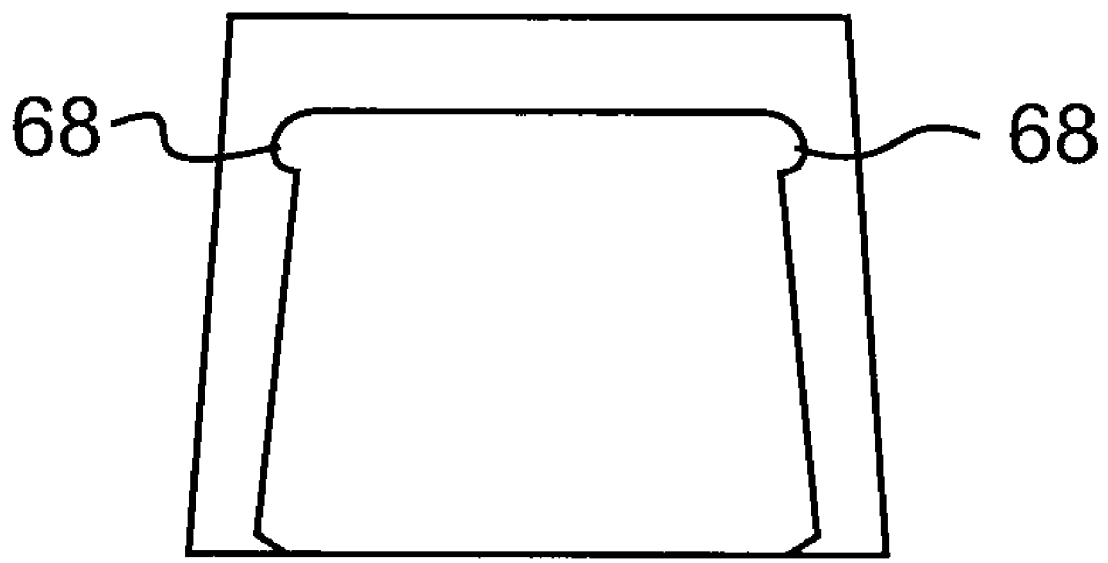

FIGS. 3-9 show embodiments of the external fixation device 16 with more details. FIGS. 4-7 show an embodiment of the distal base portion 22 with three angled holes 26, 28, 30 to receive pins 36, 38 and 40, respectively. In this instance, the three holes extending downwardly therethrough at angles of within a range of 30 degree to 60 degree from the vertical. The holes 26, 28, 30 are each differently angled so that pins 36, 38 and 40 pass through the fracture site 14 at intersecting or crossing relationships. As shown in FIG. 3. the holes 26, 28, are also angled so that pins 36, 38 and 40 are directed downwardly towards pins 42, 44, which are angled in the opposite inward orientation from the proximal base portion 24 so as to intersect pins 36, 38, 40 when extending through the bone in the fracture site 14.

As shown in FIG. 3, the pins 42 and 44 also subtend angles within the range of 25 degrees to 60 degrees from the vertical, and form an intersecting cross-over pattern with each other and pins 36, 38 and 40 upon insertion through the fracture site 14. In one embodiment, pins 36, 38, and 40 are placed with vertical angles (i.e., the angle formed between the downward pin and the downward vertical line) of about 40, 41, and 50 degrees, respectively. Pins 42 and 44 are angled towards pins 36, 38, 40 with vertical angles of 35 and 40 degrees, respectively. A person of ordinary skill in the art would understand that these angles are exemplary only and that the fixation device 16 may have pin holes formed therethrough at various other orientations. Moreover, the number of pin holes and pins can also be modified as needed.

As shown in FIGS. 4-9, the distal base portion 22 also has a raised portion 50 on an upper surface. The raised portion 50 contains a screw-threaded aperture 51 for receiving a set screw 52 that is adapted to engage with a groove 54 of the proximal base portion 24 and to be locked thereto when the base portions 22 and 24 are in slidable engagement through the sides of the groove 54 on the proximate base portion 24 and the contacting lips 56 on the distal base portion 22.

The elongated base portions 22 and 24 both include transverse side apertures 60 for elements (not shown) for locking the pins into position in the base portions 22 and 24 upon the insertion of the pins into the bone of the patient, so as to prevent movement between the splint 20 and the pins.

The lower end portion of each base portion 22 and 24 may be provided with side slots 62 extending along partially the length of each lower side edge so that positioning spacers 48 can be slid thereon to facilitate positioning of the external fixation device. The positioning spacers 48 can be easily pulled off when the device is in its final deployed position.

In one embodiment, the positioning spacers 48 are essentially U-shaped members with slits 68 on opposite internal sides to engage with projections 70 below the side slots 62. In another embodiment, the positioning spacers 48 comprise a plastic material.

In sum, the external fixation device 16 facilitates the stabilization of open and/or unstable fractures of the distal radius, where soft tissue injury may preclude the use of alternative fracture management such as pinning, casting, and any other type of external fixation. The external fixation device 16 immobilizes the fractured distal radius without panning the wrist joint, thus allowing early wrist mobilization and avoiding ligamentotaxis. The external fixation device 16 reliably maintains fractures reduction, allows early wrist range of motion, and promotes fracture healing through direct fixation of the fracture.

The external fixation device of the present invention offer several advantages over other non-bridging fixators. First, to minimize motion of bone fragments and prevent articular step-off or deformity, it is important to achieve three-dimensional stability of all major fragments. The external fixation device of the present invention, with multiple small diameter K-wires crossing each other at different angles, greatly enhances the stability of bone fragments.

Moreover, traditional bridging and nonbridging external fixators typically use pins that are placed perpendicular to the ling axis of the bone. This configuration unloads the fracture. In contrast, the pins in the external fixation device of the present invention are more longitudinally oriented and do not unload the fracture.

In addition, the external fixation device of the present invention uses small diameter bone pins that flex when the construct is loaded and allow lead sharing across the fracture fragments, therefore facilitate callus formation and reduce the risk of nonunion. Also, the cross positioning of bone pins fixes the larger fracture fragments while buttressing the smaller fragments, helping to maintain joint congruency. The cross pin configuration works similar to reinforced concrete and the splint acts like a pillar giving rigidity to the whole device.

Finally, the external fixation device of the present invention is light weight. Despite its unilateral frame, it achieves three-dimensional stability through the multiplanar bone pin configuration.

The present invention is further illustrated by the following examples which should not be construed as limiting. The contents of all references, patents and published patent applications cited throughout this application, as well as the Figures and Tables are incorporated herein by reference.

EXAMPLES

Treatment of Distal Radius Fractures (DRF) with the Cross-Pin Fixation (CPX) System Patient Selection and Monitoring Forty-nine patients with 51 DRFs were evaluated. Among these patients, 14 patients, including 7 minors and 7 adults (AO Classification: 4, A2.1; 2, B1.1; and 1, C1.1), were treated conservatively with casting. The remaining 35 skeletally mature patients with 37 displaced extra-articular or non-displaced or displaced intra-articular DRF were treated with closed reduction and application of the CPX System. During the study, 14 patients were excluded. Among them, 12 patients were excluded for lack of either clinical and/or radiologic evaluation $\geq 12$ months, one patient was excluded for noncompliant in the early postoperative period, and another patient was excluded because his conditions necessitated the use of synthetic bone graft.

The remaining 21 patients are included in the study. The patients include 13 females, 8 males and a mean age of 54 years (age range, 27 to 87 years, see also Table 1). The fractures include 12 dominant, 7 non-dominant, and 2 mixed dominant sided injuries (see also Table 2). Mechanism of injury included 18 falls, 1 motor vehicle accident, and 2 other acute traumatic injuries. Twenty fractures were previously treated in the emergency room. Of these, six were splinted without reduction and 14 had attempted reductions. One patient was first treated at the study site. Initial consult revealed that 9 of the reduced fractures had displaced, 4 had unsatisfactory reductions, and 8 patients presented with displaced DRF. All patients consented to CRIF with Non-bridging External Fixation (the CPX System)/Possible ORIF. These patients fully understood that if the fracture was not reasonably reduced they would undergo ORIF.

The first four patients were reviewed retrospectively for the early postoperative period. When an established protocol was in place, these patients joined an otherwise prospective study. The protocol included demographics, radiographic measurements, range of motion (ROM), grip and pinch strengths, as well as scores from The Patient-Rated Wrist/Hand Evaluation (PRWHE) (MacDermid J C, et al., *J Hand Ther* 2004; 17(1): 18-23) and Disabilities of the Arm Shoulder and Hand (DASH) (Beaton D E, et al., *J Hand Ther* 2001; 14(2):128-146) which were recorded on individual client file forms using unique assigned client numbers.

The AO Classification was used to categorize fractures (Müller M E. Classification of Fractures. Berlin: *Springer-Verlag,* 1987:106-115; Müller M E (ed): *Foundation,* 1995: 1-24; Kreder H J, et al., *J Bone Joint Surg Br* 1996; 78(5): 726-731). Additional fractures included 10 ulna styloid, 1 comminuted distal ulna, and 1 displaced radial head fracture. Joint congruency of simple and complex intra-articular fractures were assessed by measuring step and gap displacement pre and postoperatively and on final x-ray examination to the nearest 0.1 mm using a ×10 magnifying loupe with an incorporated millimeter scale (B & H Specialties, Syracuse, N.Y.) (Cole R. J et al., *J Hand Surg,* 1997; 22(5):792-800); Kreder H J, et al., *J Hand Surg,* 1996; 21(1):31-39).

Radiographic measurements were performed by an independent radiologist using Digimizer image analysis software, version 3.4.1 (MedCalc Software, Belgium). An independent x-ray technician digitized the pre-op, initial post-op and final radiographs, and copied them in their respective groups on separate CD's. The radiographs were not viewed side by side. The radiologist, blinded to the demographics of the study population was given one group at a time to measure and record RI, RH, PT, and UV.

All surgical procedures were performed by the investigating physician at an out patient ambulatory facility. All patients provided authorization to participate in this study. There were no conversions to ORIF. For removal of hardware, patients were given the choice of undergoing removal either in the office or at an ambulatory facility. This study was not submitted to an Institution Review Board.

Surgical Technique

Figure 14:
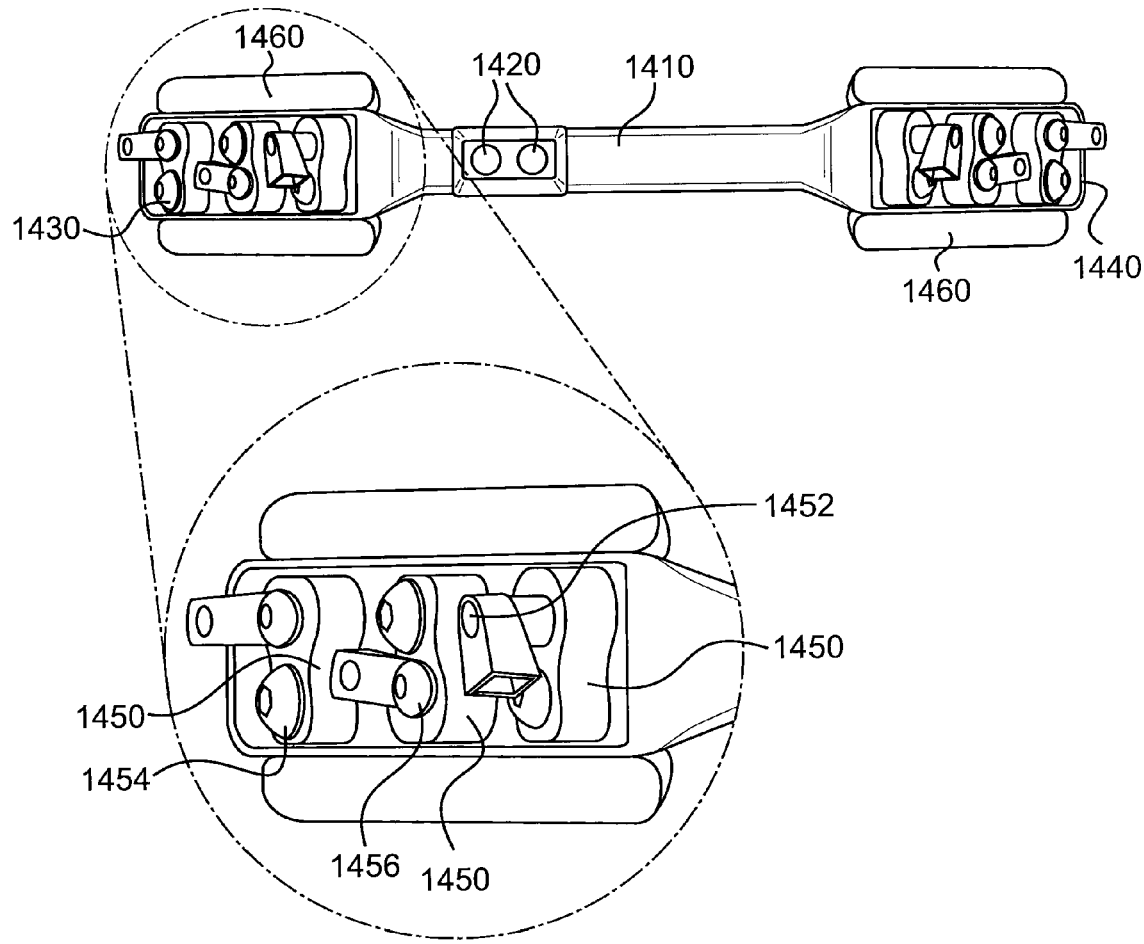
FIG. 14 is a picture of the CPX device used in Example 1.

The CPX device (FIG. 14) is made of aluminum and is light-weight (41 grams, with the pins). It consists of a two-part sliding bar 1410 with two screws 1420 to adjust the length (11.5 to 14.5 cm). At either end of the sliding bar 1410 are two heads 1430 and 1440, each with three adjustable K-wire fixators 1450. Each of the K-wire fixators 1450 has a K-wire guide hole 1452, an angle locking screw 1454 that controls the angle of insertion of the K-wire (not shown). Skin spacers 1460 are attached to the heads 1430 and 1440 to maintain the proper distance between the sliding bar 1410 and the forearm during the assembly of the CPX device. The skin spacers 1460 are removed once the CPX device is assembled and fixated. From a technical standpoint, the device allows 10 degrees of rotation of the K-wire around the center insertion point. All the screws of the CPX device are loosened prior to reduction of the fracture.

Surgery was performed under either regional IV block (4 patients) or axillary block (17 patients) under fluoroscopic control. The fractures were reduced by using the classical maneuver; palmar flexion and ulnar deviation (MacDermid J C, et al., *BMC Musculoskelet Disord*, 2003; 31; 4:24) or by applying longitudinal traction with finger traps. After confirmation of reduction using a FlouroScan in the AP and lateral planes, a small stab wound was made near the radial styloid between the first and second dorsal compartments. A clamp was used to spread the soft tissues and a tissue protector was introduced into the incision and held against the bone at a 40 to 45° angle. All K-wires were smooth 1.6 mm. The first K-wire was then driven obliquely across the fracture site. While driving this K-wire, dorsal pressure was applied on the distal fragment to maintain PT while the wrist is held in ulnar deviation to maintain RI. The K-wire should exit the proximal fragment (radial shaft) in a mid-lateral plane. The first K-wire was then placed through the distal most K-wire fixator in the device.

Figure 15A:
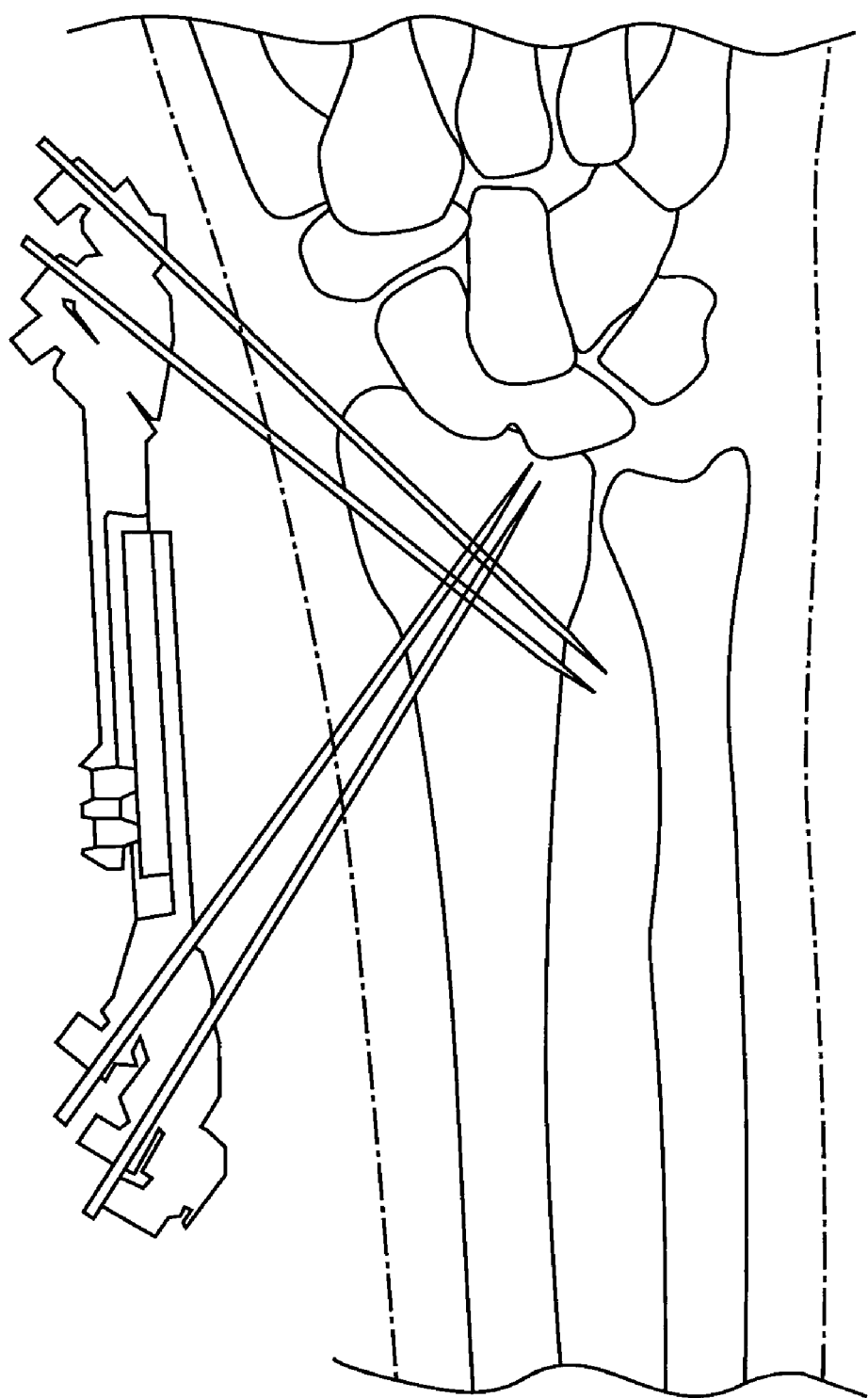
FIGS. 15A and 15B are radiographs of a DRF with the CPX device.
Figure 15B:
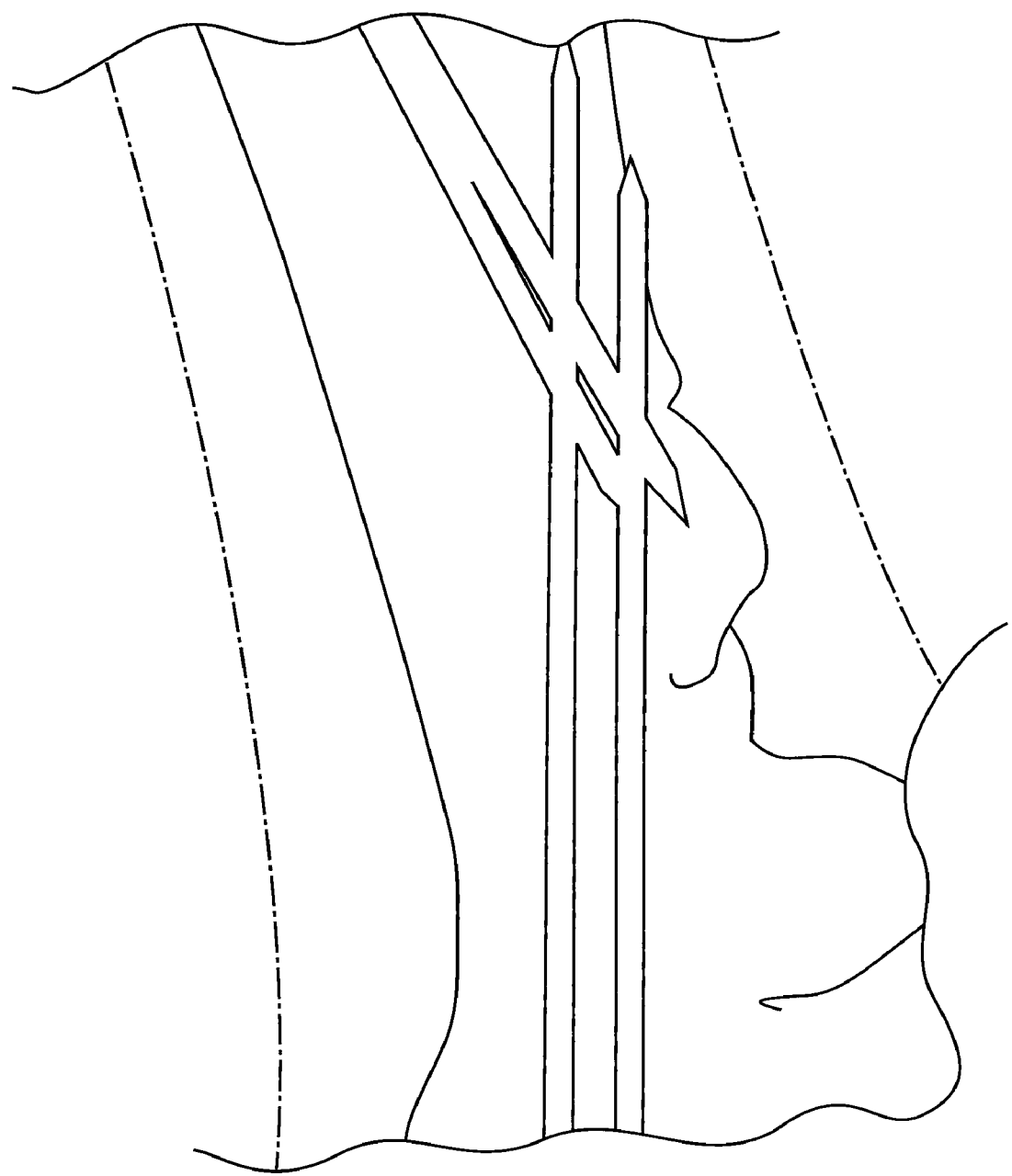

The CPX device was then aligned with the distal forearm in the mid-lateral plane. A second K-wire, also using a tissue protector, was then inserted through the proximal K-wire fixator, aiming at the lunate fossa. A small stab wound was made and a clamp was used to spread the soft tissues to facilitate the introduction of the tissue protector. The K-wire angle of insertion can be varied ±10 degrees on-center to achieve the desired position. The remaining K-wires were then introduced in a similar manner using a minimum of 2 distally and 2 proximally (FIG. 15). Intra-articular displaced fractures did not require fragment-specific fixation as the percutaneous pinning and cross-pin fixation of the fractures with the CPX device maintained reduction.

After surgery, patients were placed in soft dressings with a short arm volar splint and instructed to perform active finger range of motion (ROM). Patients were initially seen post-operatively for (1) removal of the surgical dressing, (2) radiographic evaluation, (3) pin site care, (4) assessment and reinforcement of active finger ROM, and (5) fabrication of a custom wrist/forearm orthosis by the investigating Occupational Therapist (OT). Occupational therapy, three times per week, commenced immediately thereafter to initiate additional active finger ROM, wrist and forearm active range of motion (AROM), a formal home exercise program, and resumption of usual activities. Patients were instructed to remove the splint six times each day to perform their home exercise program. Pin care management was rendered during office visits by applying hibiclens-soaked gauze wraps to the pin sites.

Assessment Parameters

Radiographs were taken at 2, 4, 6, 8, 12 weeks, 6 months, 1 year or longer post-surgery to assess radiological parameters of RI, RH, PT, and UV. Posterior-anterior (PA) views were performed with the forearm in pronation and lateral views with the forearm in neutral position. The CPX device and K-wires were removed once bone healing was verified by radiographic observation of trabecular bridging across the fracture site and obliteration of distinct fracture lines. From the initial to final post-op radiographic examination, maintenance of fracture reduction was defined as a loss of less than 5° RI, less than 2 mm RH, less than 10° PT (Knirk J L, et al., *J Bone Joint Surg*, 1986; 68(5):647-659; McQueen M, et al., *J Bone Joint Surg*, 1988; 70B: 649-651) or an increase in ulnar variance greater than 1.5 mm.

At designated intervals, the OT recorded goniometric wrist measurements in flexion, extension, pronation, supination, and radial and ulnar deviation as well as, grip and pinch strengths using the Jamar hydraulic hand dynamometer (Lafayette Instrument Company, Lafayette, Ind.) and the Baseline hydraulic pinch gauge (FEI, Irvington, N.Y.). These values were recorded on custom designed occupational therapy forms. The findings were compared with the contralateral side. Scar assessment for height (flat, hypertrophic or keloid) and mobility (mobile, adhesion: minimum, moderate or severe) were also recorded on the forms. Wrist rehab was determined by calculating the number of days from each patient's surgery to their initial therapy evaluation.

Patients completed the initial self-administered PRWHE (MacDermid J C, et al., *J Orthop Trauma*, 1998; 12(8):577-586; MacDermid J C, et al., *J Hand Surg*, 2000; 25(2):330-340) and the DASH (Solway S, et al., *Institute for Work and Health*, 2002:1-22) instruments during their initial therapy evaluation. The PRWHE was obtained at 4, 6, 8, and 12 weeks, 6 months, and again at 1 year and/or final evaluation. Early in the study, a follow-up DASH was obtained at 3 and 6 months and one year. Later, an 8-week and then a 4-week DASH were added. These instruments provided outcome measurements of physical function, symptoms (pain), disability, appearance, and return to usual activities.

Descriptive measurements (mean (standard deviation (SD)); median (range) were used to tabulate the pre- and post-surgical parameters of radiologic measurements, grip and pinch strength, AROM, DASH, and PRWHE scores. Data was not available for all patients at all time points. The percentages shown are the results for the number of available patients in each parameter and time point. Comparisons between injured and non-injured hands/wrists serve as controls for each patient's individual post-operative outcome. Data was collected at baseline (initial post-operative evaluation with the OT); 2, 4, 6, 8, and 12 weeks; 6 months; and 1 year or more post-surgery.

Table 1 reports demographic, clinical and outcome characteristics of the study population. Mean follow-up was 20 months (range, 12 to 36 m). Table 2 shows the AO classification of the distal radius fractures. All fractures were reduced by closed reduction with no conversions to open. Patients were seen a mean of 6 days (range, 3 to 12 d) post surgery for radiographs and application of a removable custom orthosis. Table 3 shows normal radiographic parameters and longitudinal radiographic measurements of the study population (Fernandez D L, et al., Springer-Verlag, 2002:58-60; Azegami S., 2008). Preoperatively the mean, intra-articular step was 0.5 mm (SD 0.7) and the gap was 1.2 mm (SD 1.1). On final evaluation there were no step-offs, the mean gap was 0.2 mm (SD 0.4).

Preoperative mean radiographic measurements were RI 20.9±5.4°, RH 8.5±4.4 mm, PT −2.7±13.7°, and UV 2.2±2.9 mm. At the initial post-op visit, mean radiographic results were RI 24.9±3.3°, RH 10.9±2.6 mm, PT 5.4±4.1°, and UV 0.6±2.2 mm. Three patients (#5, 6, and 16) were not fully restored; lacking RH or PT. Final mean measurements revealed RI 25±3.6°, RH 11±2.47 mm, PT 5.1±4.1° and UV 0.8±2 mm. UV was greater than 2 mm in 6 patients and greater than −2 mm in 2 patients. Comparison of the initial post-op radiographic measurements to final revealed no loss of reduction (Table 3).

TABLE 1

Clinical and Outcome Characteristics of Study Population

| Pt* No.* | Sex, Age y* | Injured Side, Dominance | AO Class* | Associated Injuries | Prior Rx* | No.* Pins Distal/ Proximal | Othosis Applied (d)* |
|---|---|---|---|---|---|---|---|
| 1 | F, 56 | L, ND | C2.2 | None | ACR*, SAC* | 3/2 | 6 |
| 2 | F, 38 | R, D | C2.1 | None | ACR*, S-TS* | 3/2 | 6 |
| 3 | M, 36 | L, ND | C3.1 | None | ACR*, S-TS* | 4/2 | 5 |
| 4 | M, 54 | R, D | B3.1 | None | ACR*, S-TS* | 3/2 | 6 |
| 5 | F, 68 | R, D | C1.1 | None | ACR*, SAC* | 4/2 | 3 |
| 6 | F, 55 | L, D | C1.1 | None | ACR*, S-TS* | 3/2 | 7 |
| 7 | M, 45 | R, D | B2.2 | Neck and Shoulder | Cast | 3/2 | 5 |
| 8 | F, 71 | R, D | C1.1 | None | Splint | 2/2 | 8 |
| 9 | M, 87 | L, M | C1.1 | Fracture: Ulna Shaft, Elbow | ACR*, SAC* | 3/2 | 8 |
| 10 | F, 57 | L, D | A2.2 | None | Splint | 3/2 | 8 |
| 11 | F, 56 | L, D | A2.2 | None | ACR* S-TS* | 3/2 | 8 |
| 12 | F, 55 | R, D | B3.3 | None | ACR*, SAC* | 3/2 | 8 |
| 13 | M, 33 | L, M | C2.1 | Multiple Trauma | ACR*, S-TS* | 3/2 | 5 |
| 14 | F, 29 | L, ND | C2.2 | None | Splint | 2/2 | 6 |
| 15 | M, 55 | L, ND | C3.1 | None | ACR*, S-TS* | 2/2 | 6 |
| 16 | F, 65 | R, D | C2.1 | None | ACR*, S-TS* | 2/2 | 6 |
| 17 | M, 27 | L, D | C3.1 | None | SAC* | 2/2 | 6 |
| 18 | F, 72 | R, ND | C1.1 | None | Splint | 2/2 | 4 |
| 19 | F, 48 | L, ND | C1.1 | None | None | 2/2 | 3 |
| 20 | M, 63 | L, ND | C1.1 | None | ACR*, S-TS* | 2/2 | 5 |
| 21 | M, 54 | R, D | A2.2 | None | ACR*, SAC | 2/2 | 5 |

| Pt* No.* | Wrist Rehab Began (d)* | HW* d/c* (d)* | Complications (r)* | Final FU* (m)* | PRWHE* | DASH* | Grip Strength of Un Rx* (%)* |
|---|---|---|---|---|---|---|---|
| 1 | 13 | 44 | | 36 | 6.5 | 2.5 | 91 |
| 2 | 10 | 45 | | 16 | 25 | 5 | 108 |
| 3 | 9 | 40 | | 25 | 0 | 0 | 109 |
| 4 | 7 | 61 | | 33 | 4.5 | 3.3 | 109 |
| 5 | 4 | 45 | DSBRN* | 31 | 0 | 0 | 90 |
| 6 | 14 | 48 | | 29 | 1 | 0 | 92 |
| 7 | 8 | 40 | CRPS* (r) | 26 | 5.5 | 6.7 | 109 |
| 8 | 12 | 44 | | 22 | 1.5 | 6.7 | 102 |
| 9 | 15 | 44 | | 22 | 0 | 3.3 | 70 |
| 10 | 9 | 43 | | 21 | 8 | 10 | 112 |
| 11 | 15 | 47 | | 21 | 1 | 0 | 102 |
| 12 | 16 | 43 | | 18 | 31.5 | 22 | 69 |
| 13 | 13 | 54 | CTS* (r)* s/p* ECTR* Wrist stiffness Rx* manipulation | 17 | 43 | 28 | 28 |
| 14 | 12 | 47 | | 12 | 8.5 | 4.2 | 84 |
| 15 | 9 | 41 | | 14 | 7 | 4.2 | 72 |
| 16 | 7 | 45 | | 12 | 1.5 | 7.5 | 131 |
| 17 | 10 | 45 | | 12 | 1 | 2.5 | 83 |
| 18 | 7 | 39 | | 12 | 0 | 2.5 | 110 |
| 19 | 12 | 46 | | 12 | 7.5 | 10 | 65 |
| 20 | 9 | 48 | | 12 | 32 | 26 | 55 |
| 21 | 8 | 43 | | 12 | 0 | 0 | 103 |

*Pt., patient; *No., number; *y, year; Class., classification; *Rx., treatment; *d, days; *HW, hardware, (removed); *d/c. discontinued; *r, resolved; *FU, Followup; *m, mouth; *PRWHE, Patient rated wrist hand evaluation; *DASH, disabilities of the arm, shoulder and hands; *un Rx, unaffected side; *%, percentage; ACR, attempted dosed reduction; *SAC, short arm cast; *S-TS, sugar-tong splint; *DSBRN, dorsal sensory branch radial nerve; *CRPS, complex regional pain syndrome; *CTS, carpal tunnel syndrome; *s/p, status post; *ECTR, endoscopic carpal tunnel release

TABLE 2

Distribution of Distal Radius Fractures According to AO Classification

| | Fracture Type | Type | No.[a] | Percent[b] |
|---|---|---|---|---|
| A- | Extra-articular | A2.2 | 3 | 14.0 |
| B- | Simple articular | B2.2 | 1 | 5.0 |
| | | B3.1 | 1 | 5.0 |
| | | B3.3 | 1 | 5.0 |
| C- | Complex articular | C1.1 | 7 | 33.0 |
| | | C2.1 | 3 | 14.0 |
| | | C2.2 | 2 | 10 |
| | | C3.1 | 3 | 14.0 |
| | Total DRF | | 21 | |

[a]No., number of fractures treated per classification.
[b]Percent, percentage of each DRF classification treated.

All fractures healed with removal of the CPX device and K-wires at an average of 45 days (range, 39 to 61 days) postoperatively. One patient had removal of hardware in the office, the remaining patients elected to return to the ambulatory facility for removal of hardware under sedation. With this second procedure, there were no complications.

Table 4 shows the final PRWHE subscale for Appearance of the wrist/hand on a scale of zero to 10, with zero being no dissatisfaction and 10 being complete dissatisfaction. Fourteen patients (67%) expressed no dissatisfaction. The remaining 7 patients (33%) expressed dissatisfaction to a value no greater than 3. Final OT evaluation of scar height revealed all proximal and distal scars were flat. Evaluation for scar mobility revealed 38 were mobile with 1 proximal and 3 distal having mild adhesions.

TABLE 3

Radiographical Measurements[a]

| | Pre-op | | | | | | Initial Post-Op Visit | | | | | | Final Evaluation | | | | | |
|---|---|---|---|---|---|---|---|---|---|---|---|---|---|---|---|---|---|---|
| Pt. No. | RI[b] | RH[c] | PT[b] | Uv[c] | Step[c] | Gap[c] | RI[b] | RH[c] | PT[b] | UV[c] | Step[c] | Gap[c] | RI[b] | RH[c] | PT[b] | UV[c] | Step[c] | Gap[c] |
| 1 | 21 | 3.1 | −31 | 5.6 | 0 | 2.5 | 25.5 | 11.5 | 0 | 0 | 0 | 0.7 | 26.6 | 12.8 | 0.8 | 0 | 0 | 0.7 |
| 2 | 8.7 | 0 | −38 | 4 | 0 | 0.5 | 20.3 | 11.1 | 7.8 | −2.4 | 0 | 0 | 20.1 | 10.6 | 7.4 | −2 | 0 | 0 |
| 3 | 21.2 | 10.6 | 4.3 | 3.6 | 1.6 | 2 | 23.9 | 12.3 | 1.1 | 1.1 | 0 | 0 | 13.3 | 11.9 | 0.7 | 1.6 | 0 | 0 |
| 4 | 26.2 | 13.4 | 5.5 | 0.8 | 1.7 | 0.8 | 27.2 | 14.1 | 13 | −1.1 | 0 | 0 | 16.3 | 13.5 | 11.9 | −1 | 0 | 0 |
| 5 | 17.8 | 4.1 | −20.6 | 3.7 | 0 | 0.6 | 26.4 | 7.5 | −3 | 2.3 | 0 | 0.6 | 27 | 8.3 | −3.7 | 2.1 | 0 | 0 |
| 6 | 18.7 | 4.3 | 9 | 5.3 | 0 | 1 | 22.1 | 4.2 | 4.2 | 4.4 | 0 | 0 | 20.8 | 4.4 | 4.4 | 3.3 | 0 | 0 |
| 7 | 24.8 | 13 | 0 | −3 | 0.2 | 0.3 | 26.4 | 13.3 | 9.4 | −3.3 | 0.2 | 0.2 | 25.9 | 13.9 | 9.3 | −2.8 | 0 | 0 |
| 8 | 24.9 | 12.3 | −10.8 | 3.1 | 0 | 2 | 27.3 | 13.2 | 7.1 | 3 | 0 | 1 | 27.5 | 13 | 7.4 | 3 | 0 | 0 |
| 9 | 25.9 | 12.1 | 2.9 | 4.5 | 0 | 1.6 | 26.7 | 13.6 | 9.4 | 2.4 | 0 | 0 | 28.8 | 13.7 | 9.6 | 2.1 | 0 | 0 |
| 10 | 20.2 | 11 | 13.5 | −2.1 | 0 | 0 | 24.2 | 13.3 | 1.9 | −2.5 | 0 | 0 | 22.8 | 13.4 | 1.7 | −1.8 | 0 | 0 |
| 11 | 27 | 12 | 3.3 | 1.6 | 0 | 0 | 29.3 | 13.3 | 7.4 | 0 | 0 | 0 | 28.4 | 13 | 7.1 | 0 | 0 | 0 |
| 12 | 14 | 0 | −4.5 | 0 | 1 | 3 | 20.3 | 11 | 5.4 | 0 | 0 | 1 | 25 | 10.7 | 4.4 | 0 | 0 | 1 |
| 13 | 22.2 | 13.4 | 0 | 1.7 | 14 | 1.7 | 23.2 | 10.3 | 0 | 0 | 0 | 0 | 23.3 | 11.1 | 0 | 0 | 0 | 0 |
| 14 | 18 | 4.9 | 3.7 | 1.9 | 0 | 1 | 26.1 | 10.3 | 9.5 | 0 | 0 | 0 | 25.9 | 9.8 | 9.4 | 1.4 | 0 | 0 |
| 15 | 18.2 | 4.2 | −4.6 | 5.6 | 2 | 3.5 | 24.7 | 9.3 | 5 | 2 | 0 | 2 | 23.2 | 9.7 | 4.1 | 1.9 | 0 | 1.5 |
| 16 | 23.1 | 6.3 | 11 | 6.3 | 0.5 | 2 | 26.2 | 6.9 | 9.3 | 3.9 | 0 | 0 | 27.5 | 6.8 | 10.3 | 4.4 | 0 | 0 |
| 17 | 9.9 | 11.7 | 2.9 | −4.8 | 1.6 | 2.4 | 15.8 | 11 | 0 | −2.6 | 0.8 | 0 | 14.6 | 10.6 | 0 | −2.8 | 0 | 0 |
| 18 | 30.2 | 10.4 | −5 | 2.5 | 0 | 0.2 | 28.7 | 10 | 4.7 | 1 | 0 | 0.2 | 30 | 10.56 | 3.6 | 1.8 | 0 | 0.2 |
| 19 | 25 | 10.9 | −12 | 0 | 0 | 1 | 27.4 | 10.9 | 8 | 0.8 | 0 | 1.5 | 26.2 | 10.3 | 6.7 | 1.3 | 0 | 0 |
| 20 | 21.2 | 9.3 | 3 | 3 | 0 | 1 | 22.2 | 8.6 | 7.4 | 2.8 | 0 | 0 | 22.5 | 8.8 | 8 | 3 | 0 | 0 |
| 21 | 21.6 | 10.9 | 10.1 | 2.3 | | 0 | 28.7 | 14.1 | 5.6 | 0.9 | 0 | 0 | 29 | 13.1 | 4.8 | 0.4 | 0 | 0 |
| mean | 20.9 | 8.5 | −2.7 | 2.2 | 0.5 | 1.2 | 24.9 | 10.9 | 5.4 | 0.6 | 0.05 | 0.3 | 25 | 11 | 5.1 | 0.8 | 0 | 0.2 |
| SD | 5.4 | 4.4 | 13.4 | 2.9 | 0.7 | 1.1 | 3.3 | 2.6 | 4.1 | 2.2 | 0.2 | 0.6 | 3.6 | 2.47 | 4.1 | 2 | 0 | 0.4 |
| median | 21.2 | 10.6 | 2.9 | 2.5 | 0 | 1 | 26.1 | 11 | 5.6 | 0.8 | 0 | 0.6 | 25.9 | 10.7 | 4.8 | 1.3 | 0 | 0 |
| min | 8.7 | 0 | −38 | −4.8 | 0 | 0 | 15.8 | 4.2 | −3 | −3.3 | 0 | 0 | 14.6 | 4.4 | −3.7 | −2.8 | 0 | 0 |
| max | 30.2 | 13.4 | 13.5 | 6.3 | 2 | 3.5 | 29.3 | 14.1 | 13 | 4.4 | 0.8 | 0 | 30 | 13.9 | 11.9 | 4.4 | 0 | 1.5 |

Pt., patient; No., number; RI, radial inclination; RH, radial height; PT, palmar tilt; UV, ulnar variance.
[a]normal radiological measurements (56-65): RI 22-23° (range, 13 to 30), RH 11-12 mm (range, 8 to 18), PT 11-12° (range, 0 to 20) and UV 0 mm (range, −2 to 2)
[b]measured in degrees
[c]measured in millimeters

TABLE 4

Patient Rated Wrist Hand Evaluation-Appearance[a]

| | Client Number | | | | | | | | | | | | | | | | | | | | |
|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 |
| Dissatisfaction with Appearance[b] | 0 | 1 | 0 | 0 | 0 | 0 | 0 | 1 | 0 | 0 | 0 | 1 | 3 | 1 | 2 | 0 | 0 | 0 | 0 | 2 | 0 |

[a]Patients rated their dissatisfaction with the appearance of the wrist/hand on a scale of 0 to 10.
[b]Dissatisfaction: "Rate how dissatisfied you were with the appearance of your wrist/hand during the past week."

TABLE 5

| | | Dorsiflexion | | Volarflexion | | Pronation | | Supination | |
|---|---|---|---|---|---|---|---|---|---|
| Visit | N[b] | Mean (SD) | Median (Range) | Mean (SD) | Median (Range) | Mean (SD) | Median (Range) | Mean (SD) | Median (Range) |
| IE[c] | 21 | 22 (15) | 28 (−18 to 39) | 24 (6) | 24 (8 to 36) | 69 (11) | 68 (42 to 86) | 21 (25) | 22 (−24 to 66) |
| 4 w | 20 | 36 (13) | 35 (0 to 62) | 29 (7) | 28 (16 to 42) | 75 (10) | 77 (52 to 88) | 44 (25) | 48 (−20 to 78) |
| 8 w | 19 | 46 (12) | 46 (22 to 67) | 40 (11) | 38 (20 to 70) | 80 (9) | 82 (58 to 90) | 62 (17) | 66 (20 to 82) |
| 12 w | 19 | 54 (11) | 56 (38 to 72) | 49 (11) | 50 (34 to 80) | 83 (7) | 86 (60 to 90) | 70 (14) | 74 (40 to 86) |
| 6 m | 17 | 63 (11) | 60 (40 to 78) | 58 (11) | 56 (42 to 86) | 86 (4) | 86 (76 to 90) | 79 (8) | 80 (66 to 90) |
| 1 y | 21 | 69 (11) | 71 (44 to 89) | 64 (8) | 64 (50 to 86) | 89 (2) | 90 (84 to 90) | 84 (8) | 90 (60 to 93) |

Figure 16:
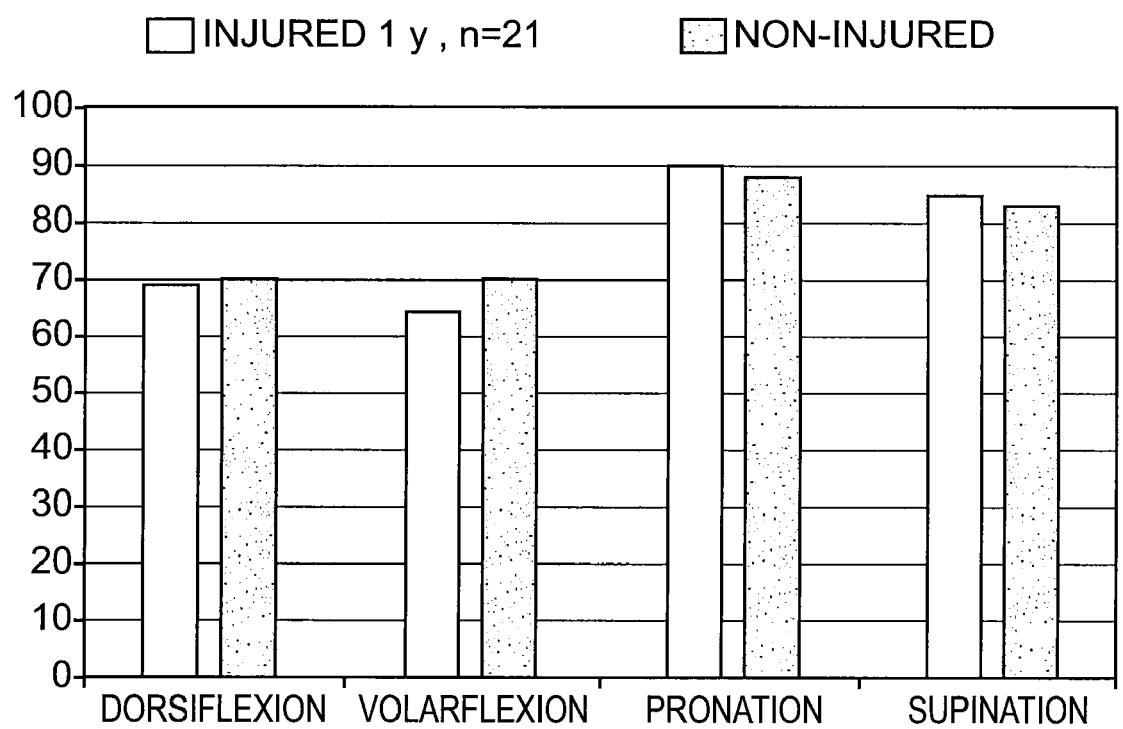
FIG. 16 is range of motion (ROM) compared to the uninjured side at final evaluation.

[a]AROM, active range of motion, measured in degrees;
[b]n, number of patients and fractures;
[c]IE, Initial post-op evaluation Formal wrist rehabilitation/mobilization began a mean of 10 days (range, 3 to 16 days) after surgery. AROM measurements by the OT revealed that the injured wrists had an initial mean dorsiflexion (DF) of 22° (29%) as compared with the uninjured wrists mean of 70°. Similarly, initial visit volar flexion (VF) of the injured wrists was 24° (34%) as compared with the uninjured wrists mean of 70° (Table 5). Both DF and VF values improved as did the abilities to pronate and supinate. In regards to AROM measurements at final evaluation, the injured side's mean scores were DF 70° (SD 11), VF 65° (SD 8), pronation 89° (SD 2), and supination 84° (SD 8). Comparison of the injured to non-injured side in percentage achieved is as follows: DF 99%, VF 92%, pronation 103%, and supination 103% (FIG. 16).

Figure 17A:
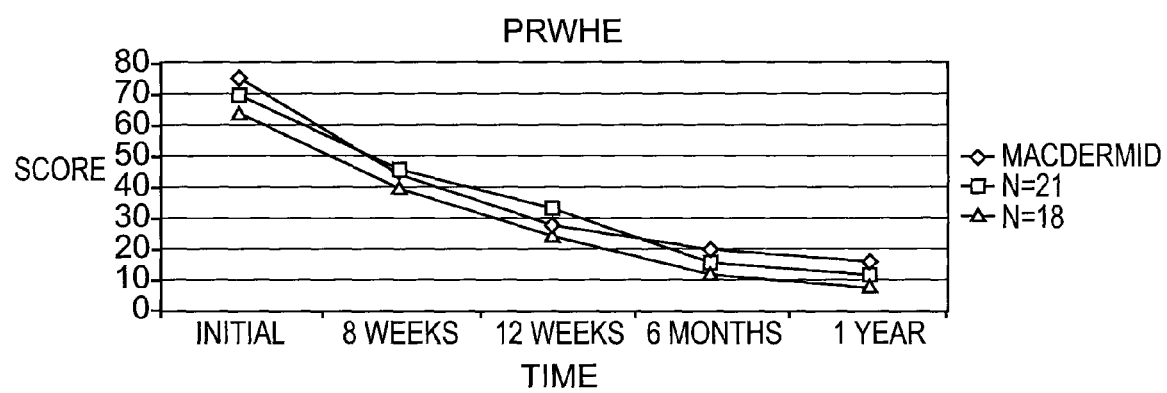
FIGS. 17A and 17B are diagrams showing mean progressive PRWHE score (FIG. 17A) and DASH score (FIG. 17B). The DASH score was compared to MacDermid's study (54); n=18, CPX patient population, eliminating 3 patients with other associated injuries.

Mean grip and lateral pinch strengths increased postoperatively relative to the uninjured hand. At 6 months, 76% of grip and 88% of pinch strength recovered, improving to 86% and 94% respectively at final evaluation (Table 6). Postoperatively, the overall mean PRWHE scores were 70 at baseline, improving to 33 at 12 weeks, and 9 at final evaluation (FIG. 17A). Within the PRWHE, the usual activities subscale (Table 7) reporting subjective difficulty in performing personal care, household work, work, and recreation revealed an overall mean subscale score of 28 (range, 4 to 40) at baseline, improving to a mean 18 (range, 0 to 39) at six weeks. The pain subscale (Table 8) reporting on four items rating disability in reference to pain as well as pain frequency revealed an overall mean subscale score of 23 (range, 2 to 49) at baseline, improving to 16 (range, 0 to 40) at six weeks. Prior to hardware removal at six weeks post surgery, mean subjective outcome of the PRWHE revealed mild pain with mild to moderate difficulty in performing usual activities with the injured hand.

Figure 17B:
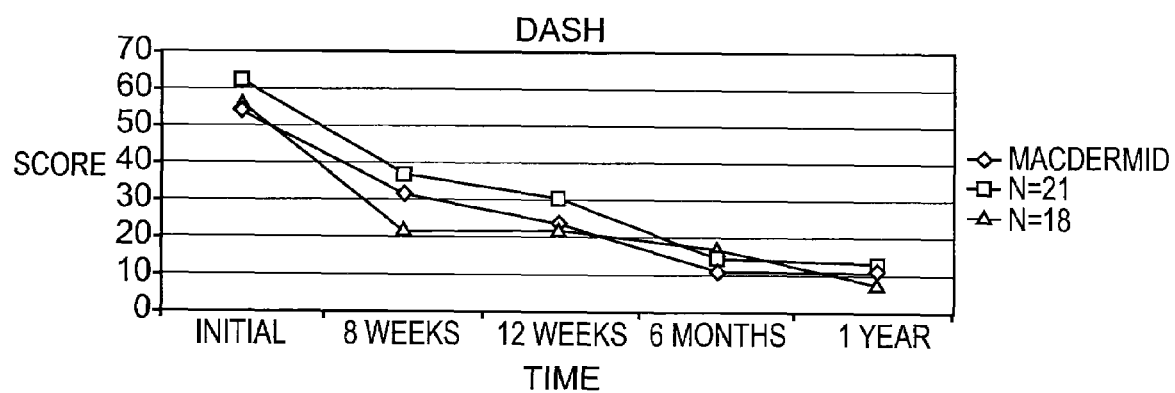

The DASH revealed that the patients had a decrease in disability and symptoms as well as an improvement in functional ability ($MDC_{95}$) when comparing baseline scores to those at 4 and 12 weeks, and again at one year (FIG. 17B). A similar functional improvement ($MDC_{95}$) was noted when comparing the baseline score to those at 8 weeks and 6 months.

One patient exhibited altered sensibility in superficial radial nerve distribution and was treated with desensitization and Gabapentin. The symptoms resolved to transient mild superficial radial nerve sensitivity without functional compromise. There were three patients with a protracted recovery. One patient, who had multiple injuries and stiffness of the wrist later developed carpal tunnel syndrome. At one year post-op, the patient underwent endoscopic carpal tunnel release and manipulation of the wrist with improvement. Another patient had associated fractures of the affected upper extremity, and the third patient with multiple injuries was diagnosed with type I complex regional pain syndrome (CRPS). Although the patient had altered sensibility in radial and ulna nerve distribution and related neck and shoulder problems, there was no allodynia or hyperpathia. These symptoms resolved, requiring no formal treatment from a pain management specialist.

TABLE 6

| | | Mean Percentage of Strength Achieved Postoperatively | | | | | |
|---|---|---|---|---|---|---|---|
| | | Grip | | | Lateral Pinch | | |
| Visit | n[a] | Injured[b] | Non-Injured[b] | Achieved[c] | Injured[b] | Non-Injured[b] | Achieved[c] |
| 8 w | 15 | 22 | 62 | 35 | 9 | 16 | 56 |
| 12 w | 19 | 33 | 61 | 54 | 13 | 17 | 76 |
| 6 m | 17 | 45 | 59 | 76 | 15 | 17 | 88 |
| FE[d] | 21 | 54 | 63 | 86 | 16 | 17 | 94 |

[a]n, number of patients and fractures;
[b]mean strength, measured in pounds;
[c]percentage of strength, in relation to the uninjured hand;
[d]FE, final evaluation.

TABLE 7

Patient Rated Wrist Hand Evaluation - Usual Activities[a]

| | | Personal Care | | Household Work | | Work or Usual Activities | |
|---|---|---|---|---|---|---|---|
| Visit | n[b] | Mean (SD) | Median (Range) | Mean (SD) | Median (Range) | Mean (SD) | Median (Range) |
| IE[c] | 16 | 6 (2) | 7 (2 to 10) | 7 (3) | 8 (2 to 10) | 8 (3) | 10 (2 to 10) |
| 4 w | 20 | 5 (3) | 5 (0 to 10) | 6 (3) | 8 (1 to 10) | 6 (4) | 6 (0 to 10) |
| 6 w | 15 | 4 (3) | 3 (0 to 9) | 4 (4) | 4 (0 to 10) | 5 (4) | 3 (0 to 10) |
| 8 w | 16 | 4 (4) | 4 (0 to 10) | 5 (3) | 5 (0 to 10) | 5 (4) | 5 (0 to 10) |
| 12 w | 15 | 2 (2) | 2 (0 to 5) | 3 (2) | 3 (0 to 5) | 3 (3) | 2 (0 to 10) |
| 6 m | 17 | 0.4 (0.7) | 0 (0 to 2) | 1 (1) | 0 (0 to 3) | 2 (3) | 0 (0 to 10) |
| FE[c] | 21 | 0.4 (0.9) | 0 (0 to 3) | 0.4 (0.8) | 0 (0 to 3) | 1 (2) | 0 (0 to 6) |

[a]Scored "0" no difficulty to "10" so difficult the patient was not able to perform the activity. Qualitative descriptors for the level of difficulty are defined as follows; 9-10 very severe, 7-8 severe, 5-6 moderate, 3-4 mild and, 1-2 minimal., 0 none;
[b]n, number of patients and fractures;
[c]IE; initial evaluation (mean of 10 days ± 3 d);
[d]FE, Final Evaluation; w, weeks; m, month; y, year.

TABLE 8

Patient Rated Wrist Hand Evaluation - Pain[a].

| | | Pain at rest | | When doing a task with repeated wrist/hand movement | | Lifting a heavy object | | When the pain is at its worst | | Frequency: How often do you have pain?[b] | |
|---|---|---|---|---|---|---|---|---|---|---|---|
| Visit | N[c] | Mean (SD) | Median (Range) | Mean (SD) | Median (Range) | Mean (SD) | Median (Range) | Mean (SD) | Median (Range) | Mean (SD) | Median (Range) |
| IE[d] | 16 | 3 (3) | 2 (0 to 9) | 6 (4) | 8 (0 to 10) | 9 (2) | 10 (3 to 10) | 6 (3) | 7 (1 to 10) | 4 (3) | 3 (1 to 10) |
| 4 w | 20 | 2 (2) | 1 (0 to 6) | 5 (3) | 4 (0 to 10) | 6 (4) | 7 (0 to 10) | 6 (3) | 5 (0 to 10) | 4 (3) | 3 (1 to 10) |
| 6 w | 15 | 1 (2) | 1 (0 to 5) | 5 (3) | 5 (0 to 10) | 7 (4) | 9 (0 to 10) | 5 (3) | 5 (0 to 10) | 2 (2) | 2 (0 to 5) |
| 8 w | 16 | 1 (1) | 1 (0 to 3) | 4 (2) | 3 (1 to 8) | 6 (3) | 7 (1 to 10) | 5 (3) | 5 (0 to 9) | 2 (2) | 2 (0 to 5) |
| 12 w | 15 | 1 (2) | 1 (0 to 6) | 3 (2.5) | 4 (0 to 9) | 4 (3) | 5 (0 to 10) | 5 (3) | 5 (0 to 10) | 3 (3) | 2 (0 to 10) |
| 6 m | 17 | 0.6 (1) | 0 (0 to 3) | 2 (2) | 1 (0 to 6) | 3 (2) | 2 (0 to 8) | 3 (3) | 2 (0 to 9) | 2 (2) | 1 (0 to 6) |
| FE[e] | 21 | 0.2 (0.5) | 0 (0 to 2) | 1 (1.5) | 1 (0 to 5) | 1 (2) | 1 (0 to 7) | 2 (2) | 1 (0 to 7) | 1 (1) | 1 (0 to 4) |

[a]Patients described their average wrist/hand symptoms over the past week using a scale of 0 to 10. Qualitative descriptors for disability items related to pain are defined as follows; (0) none, (1 to 2) minimal, (3 to 4) mild, (5 to 6) moderate, and (7 to 8) severe or (9 to 10) very severe. If the patient did not perform an activity they estimated the amount of pain or difficulty they would expect.
[b]Descriptors for pain frequency scored using a 0-10 scale are as follows: (0) none, (1-2) rarely, (3-4) occasionally, (5-6) frequent, (7-8) and (9-10) constant pain.
[c]n, number of patients and fractures;
[d]IE, Initial Evaluation;
[e]FE, Final Evaluation; w, weeks; m, months.

Figure 18:
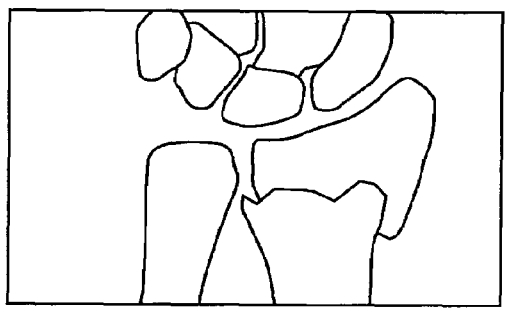
FIG. 18 shows AO classification C2.2 DRF (patient #14) treated with the CPX System. Panel A) Pre-op PA, Panel B) Pre-op lateral, Panel C) Post-op PA, Panel D) Post-op lateral, Panel E) Healed PA, and Panel F) Healed lateral.
Figure 18:
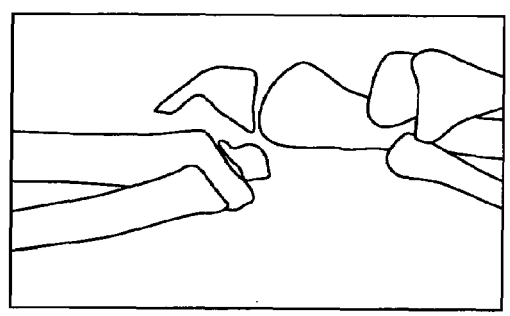
Figure 18:
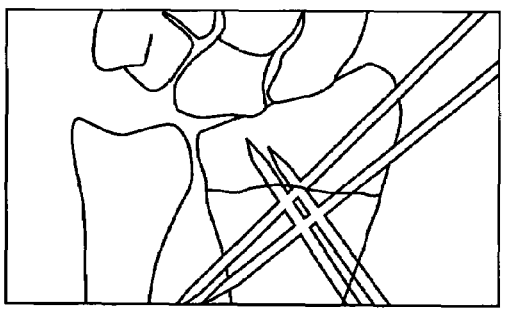
Figure 18:
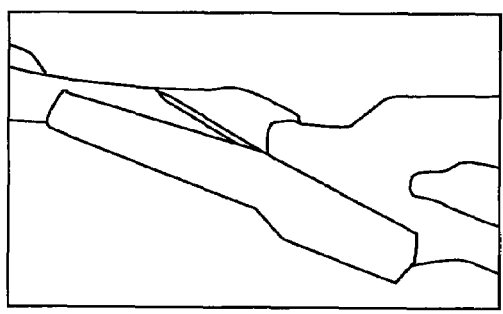
Figure 18:
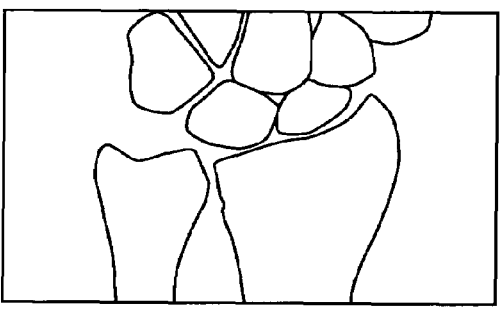
Figure 18:
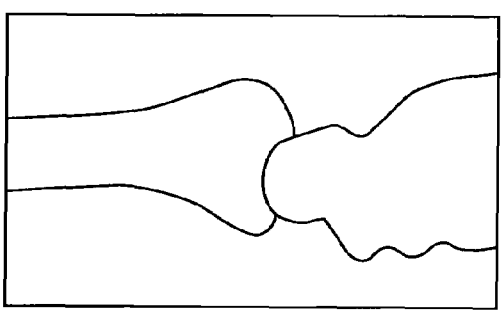

There were no pin track infections, tendon ruptures, or non-unions. In spite of the number of pins used the scars were minimal. All patients returned to their prior occupation and/or activities. FIG. 18 is an example of a C2.2 DRF pre-op, post-op and healed.

The CPX System used in this study differs substantially from other non-bridging fixators. Its unilateral frame uses smooth 1.6 mm K-wires in the mid-lateral plane. The small diameter K-wires are inserted from the radial to the ulna side of the fracture thereby crossing the fracture and each other in different planes. A multiplanar cross-pin configuration is created by using a minimum of two K-wires proximally or distally. For unstable fractures the device allows for additional K-wires. Furthermore, using a mid-lateral approach diminishes the chance of snagging extensor tendons and reduces mobility of the skin around the pins during ROM exercises and usual activities. Further, there were no pin track infections, tendonitis or tendon ruptures. The concern of using pins in the mid-lateral plane is injury to the RSN and therefore potential development of CRPS. Use of the tissue protector and intervention with Gabapentin can minimize these concerns.

The cross-pin configuration of the CPX System achieves 3-D stability, capturing larger fragments and buttressing the smaller fragments (Rogge R, et al., *J Hand Surg* 2002; 27(1): 86-92; Graham T J: In: Saffar P, Cooney W, ed. Fractures of the distal radius. 1$^{st}$ ed. London: *Martin Dunitz,* 1995:31-32). This was confirmed in this study by the fact that multi-fragment, dorsal and volar shear fractures held without supplemental or fragment specific fixation. Strauss et al (Strauss E J, *J Trauma* 2008; 64(4):975-981) substantiated the stiffness of the CPX System in a biomechanical study comparing the CPX System with a standard volar locking plate on fresh frozen human distal radii with cyclic loading of 10,000 cycles. There was no significant difference in mechanical stiffness between the two.

Based on radiographic maintenance criteria there was no loss of reduction in the study population. Although some final radiologic measurements were out of range, patients maintained reduction throughout the treatment period with early wrist mobilization and resumption of usual activities. There were no angular collapses, increases in steps and gaps, fixation failures or re-operations and all patients returned to their prior activities or employment.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. An external fixation device for the setting and corrective treatment of a bone fracture, comprising:
a splint member having a first and a second axially slidable and mutually fastenable base portions for adjusting the length of said splint member, said base portions each being rectangular in transverse cross-section so as to inhibit relative rotational displacement between said base portions while enabling axial adjustment therebetween,
wherein said first and second base portions of said splint member are each elongate bars which are axially slidably interconnected so as to extend along a common axis; and fastening structure being provided on one of said base portions for locking said other base portion thereto in predetermined axially adjusted positions,
said splint member further having axially extending grooves and cooperating lips formed extending along least a portion of the lengths of each of said base portions to facilitate adjustment of the axial length of said splint member and resulting spacing between the sets of pins between said base portions; and
a plurality of bone pins, wherein said bone pins pass through holes in each base portion of the splint member,
wherein each of said base portions of said splint member comprises mountings for said bone pins to traverse the site of the bone fracture in a multi-angle and multi-planar configuration so as to secure fractured bone segments against rotation and axial movement, and
further wherein positioning spacers are detachably mounted on the outer ends of said base portions to facilitate the radial spacing of said device relative to the forearm of a patient during the deployment of the splint member for fixation of the fracture site, wherein said positioning spacers are arranged so as to be mounted on grooves formed in lower side edges of each said based portion, and are axially slidably detachable upon completion of the deployment of said splint member proximate said fracture site, and
wherein said splint member comprises a fiber reinforced polymeric material.

2. The external fixation device of claim 1, wherein said polymeric material is selected from the group consisting of PPS (polyphenylene sulfide), PEEK (polyetherether ketone), Ultrapek (polyether ketone ether ketone), epoxy, polyester, polyamide, and vinyl ester.

3. The external fixation device of claim 1, wherein said fiber is selected from the group consisting of carbon fibers, glass fibers, metal fibers, synthetic fibers, and mixtures thereof.

4. The external fixation device of claim 1, wherein said fiber reinforced polymeric material comprises carbon-fiber reinforced plastic.

5. The external fixation device of claim 4, wherein said carbon-fiber reinforced plastic has a minimal tensile strength equal to or greater than 30 Ksi.

6. The external fixation device of claim 4, wherein said carbon-fiber reinforced plastic is PPS reinforced with 40-60% of carbon fiber.

7. The external fixation device of claim 4, wherein said carbon-fiber reinforced plastic is PEEK reinforced with 30-50% of carbon fiber.

8. The external fixation device of claim 4, wherein said carbon-fiber reinforced plastic is epoxy reinforced with 30-60% of carbon fiber.

9. The external fixation device of claim 1, wherein said first base portion of said splint comprises a proximal base segment and said second base portion of said splint comprises a distal base segment proximate the distal radius head of the forearm; each set of said bone pins including a specified number of bone pins.

10. The external fixation device of claim 9, wherein said proximal base segment mounts two of said bone pins and said distal base segment mounts three of said bone pins.

11. The external fixation device of claim 10, wherein said three base pins in said distal base segment subtend angles relative to the normal extending through said splint member and into said fracture site within a range of about 30° to 60°.

12. The external fixation device of claim 11, wherein the bone pin located towards the outer end of said distal base segment subtends an angle of about 40°, the second bone pin located axially inward thereof subtends an angle of about 41°, and the third bone pin which is furthermost axially inward subtends an angle of about 50° relative to a normal.

13. The external fixation device of claim 10, wherein said two bone pins in said proximal base segment subtend angles relative to the normal extending through said splint member and into said fracture site within a range of about 25° to 60°.

14. The external fixation device of claim 13, wherein the bone pin located towards the outer end of said proximal base segment subtends an angle about 35° and the second base pin located axially inwardly subtends an angle of about 40° relative to a normal.

15. The external fixation device of claim 1, wherein said fastening structure comprises at least one set screw for locking said base portions in predetermined axial adjustment relative to each other.

16. The external fixation device of claim 1, wherein said bone pins are each constituted of a surgical-grade metal.

17. The external fixation device of claim 1, wherein said bone pins comprise standard Kirschner wires (K-wires).

18. An external fixation device for the setting and corrective treatment of a bone fracture, comprising:
a splint member having a first and a second axially slidable and mutually fastenable base portions for adjusting the length of said splint member; and
a plurality of bone pins, wherein said bone pins pass through holes in each base portion of the splint member, wherein the base portions comprise transverse side apertures for elements for locking the pins into position in the base portions upon the insertion of the pins into the bone of the patient,
further wherein each of said base portions of said splint member comprises mountings for said bone pins to traverse the site of the bone fracture in a mutually crossing and intersecting pin arrangements so as to secure fractured bone segments against rotation and axial movement, and
wherein said splint member is made from carbon fiber reinforced plastic with a minimal tensile strength equal to or greater than 30 Ksi.

19. An external fixation device for the setting and corrective treatment of a bone fracture, comprising:
a splint member having a first and a second axially slidable and mutually fastenable base portions for adjusting the length of said splint member; and
a plurality of bone pins, wherein said bone pins pass through holes in each base portion of the splint member, wherein the base portions comprise transverse side apertures for elements for locking the pins into position in the base portions upon the insertion of the pins into the bone of the patient, further wherein each of said base portions of said splint member comprises mountings for said bone pins to traverse the site of the bone fracture in a mutually crossing and intersecting pin arrangements so as to secure fractured bone segments against rotation and axial movement, and wherein said splint member is made from a high strength material.

20. The external fixation device of claim 19, wherein said high strength material is mineral reinforced plastic.

21. The external fixation device of claim 20, wherein said mineral is selected from the group consisting of talc, silica, silicon carbide, zirconia and alumina.

22. The external fixation device of claim 19, wherein said high strength material is a ceramic material.

23. The external fixation device of claim 22, wherein said ceramic material is selected from the group consisting of alumina, zirconia, and silicon carbide.

24. The external fixation device of claim 19, wherein said high strength material is steel or steel alloys.

25. A method for treating distal radius fracture, said method comprising:
  inserting a first bone pin through the fracture site;
  joining a first base portion of a splint member of the external fixation device of claim 1 with the first bone pin;
  inserting a second bone pin through the fracture site;
  joining a second base portion of the splint member with the second bone pin;
  positioning and joining the first base portion with the second base portion of the splint member; and
  inserting one or more bone pins into the fracture site through the first base portion, the second base portion, or both base portions of the splint member, wherein said bone pins pass through holes in each base portion of the splint member,
  wherein the bone pins traverse the site of the bone fracture in a multi-angle and multi-planar configuration so as to secure fractured bone segments against rotation and axial movement, and wherein said splint member is made of a reinforced lightweight polymeric material.

26. The method of claim 25, wherein said polymeric material is selected from the group consisting of PPS (polyphenylene sulfide), PEEK (polyetherether ketone), Ultrapek (polyether ketone ether ketone), epoxy, polyester, polyamide, and vinyl ester.

27. The method of claim 26, wherein said polymeric material is reinforced with a material selected from the group consisting of carbon fibers, glass fibers, metal fibers, synthetic fibers, minerals and mixtures thereof.

28. The method of claim 27, wherein said minerals is selected from the group consisting of talc, silica, silicon carbide, zirconia and alumina.

29. The method of claim 25, wherein said reinforced polymeric material comprises carbon-fiber reinforced plastic with a minimal tensile strength of about 30 Ksi.

30. The method of claim 25, wherein said splint member allows for insertion of up to six bone pins into the fracture site.

31. An external fixation device for the setting and corrective treatment of a bone fracture in a patient, comprising:
  a splint member having a first and a second axially slidable and mutually fastenable base portions for adjusting the length of said splint member; and
  a plurality of bone pins, wherein said bone pins pass through holes in each base portion of the splint member, wherein the base portions comprise transverse side apertures for elements for locking the pins into position in the base portions upon the insertion of the pins into the bone of the patient, further wherein each of said base portions of said splint member comprises mountings for said bone pins to traverse the site of the bone fracture in a multi-angle and multi-planar configuration so as to secure fractured bone segments against rotation and axial movement, and wherein said splint member comprises a fiber reinforced polymeric material.

32. A method for treating distal radius fracture, said method comprising:
  inserting a first bone pin through the fracture site;
  joining a first base portion of a splint member of the external fixation device of claim 18 with the first bone pin;
  inserting a second bone pin through the fracture site;
  joining a second base portion of the splint member with the second bone pin;
  positioning and joining the first base portion with the second base portion of the splint member; and
  inserting one or more bone pins into the fracture site through the first base portion, the second base portion, or both base portions of the splint member, wherein said bone pins pass through holes in each base portion of the splint member,
  wherein the bone pins traverse the site of the bone fracture in a multi-angle and multi-planar configuration so as to secure fractured bone segments against rotation and axial movement, and wherein said splint member is made of a reinforced lightweight polymeric material.

33. A method for treating distal radius fracture, said method comprising:
  inserting a first bone pin through the fracture site;
  joining a first base portion of a splint member of the external fixation device of claim 19 with the first bone pin;
  inserting a second bone pin through the fracture site;
  joining a second base portion of the splint member with the second bone pin;
  positioning and joining the first base portion with the second base portion of the splint member; and
  inserting one or more bone pins into the fracture site through the first base portion, the second base portion, or both base portions of the splint member, wherein said bone pins pass through holes in each base portion of the splint member,
  wherein the bone pins traverse the site of the bone fracture in a multi-angle and multi-planar configuration so as to secure fractured bone segments against rotation and axial movement, and wherein said splint member is made of a reinforced lightweight polymeric material.

34. A method for treating distal radius fracture, said method comprising:
  inserting a first bone pin through the fracture site;
  joining a first base portion of a splint member of the external fixation device of claim 31 with the first bone pin;
  inserting a second bone pin through the fracture site;
  joining a second base portion of the splint member with the second bone pin;
  positioning and joining the first base portion with the second base portion of the splint member; and
  inserting one or more bone pins into the fracture site through the first base portion, the second base portion, or both base portions of the splint member, wherein said bone pins pass through holes in each base portion of the splint member, wherein the bone pins traverse the site of the bone fracture in a multi-angle and multi-planar configuration so as to secure fractured bone segments against rotation and axial movement, and wherein said splint member is made of a reinforced lightweight polymeric material.

* * * * *